US009629914B2

(12) United States Patent
DeAngelis

(10) Patent No.: US 9,629,914 B2
(45) **Date of Patent: *Apr. 25, 2017**

(54) HEPAROSAN-BASED BIOMATERIALS AND COATINGS AND METHODS OF PRODUCTION AND USE THEREOF

(71) Applicant: The Board of Regents of the University of Oklahoma, Norman, OK (US)

(72) Inventor: Paul L. DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 284 days.

This patent is subject to a terminal disclaimer.

(21) Appl. No.: 14/060,077

(22) Filed: Oct. 22, 2013

(65) Prior Publication Data

US 2014/0155497 A1 Jun. 5, 2014

Related U.S. Application Data

(63) Continuation of application No. 12/080,060, filed on Mar. 31, 2008, now Pat. No. 8,580,290, and a continuation-in-part of application No. 11/906,704, filed on Oct. 3, 2007, now Pat. No. 8,088,604, and a continuation-in-part of application No. 11/651,379, filed on Jan. 9, 2007, now Pat. No. 7,579,173, which is a continuation of application No. 10/642,248, filed on Aug. 15, 2003, now Pat. No. 7,223,571, and a continuation-in-part of application No. 10/195,908, filed on Jul. 15, 2002, now abandoned, which is a continuation-in-part of application No. 10/142,143, filed on May 8, 2002, now Pat. No. 7,307,159.

(60) Provisional application No. 60/921,296, filed on Mar. 30, 2007, provisional application No. 60/849,034, filed on Oct. 3, 2006, provisional application No. 60/404,356, filed on Aug. 16, 2002, provisional application No. 60/479,432, filed on Jun. 18, 2003, provisional application No. 60/491,362, filed on Jul. 31, 2003, provisional application No. 60/289,554, filed on May 8, 2001.

(51) Int. Cl.

| | |
|---|---|
| ***A61K 47/36*** | (2006.01) |
| ***A61K 9/00*** | (2006.01) |
| ***C07H 5/04*** | (2006.01) |

(52) U.S. Cl.

CPC ............ *A61K 47/36* (2013.01); *A61K 9/0024* (2013.01); *C07H 5/04* (2013.01)

(58) Field of Classification Search

CPC .............................. A61K 9/0024; A61K 47/36

See application file for complete search history.

(56) References Cited

U.S. PATENT DOCUMENTS

| | | | | |
|---|---|---|---|---|
| 5,314,876 | A * | 5/1994 | Lormeau | C08B 37/0075 514/56 |
| 5,384,398 | A | 1/1995 | Lormeau et al. | |
| 5,470,911 | A | 11/1995 | Rhee et al. | |
| 5,550,187 | A * | 8/1996 | Rhee | G02B 1/043 424/423 |
| 5,756,553 | A * | 5/1998 | Iguchi | A61L 27/54 424/425 |
| 5,827,937 | A | 10/1998 | Agerup | |
| 5,876,433 | A | 3/1999 | Lunn | |
| 5,958,899 | A | 9/1999 | Zoppetti et al. | |
| 6,120,536 | A | 9/2000 | Ding et al. | |
| 6,156,373 | A | 12/2000 | Zhong et al. | |
| 6,162,797 | A | 12/2000 | Zoppetti et al. | |
| 6,444,447 | B1 | 9/2002 | DeAngelis | |
| 7,244,270 | B2 | 7/2007 | Lesh | |
| 7,291,673 | B2 | 11/2007 | Hubbell et al. | |
| 7,307,159 | B2 | 12/2007 | DeAngelis | |
| 7,771,981 | B2 | 8/2010 | DeAngelis | |
| 8,088,604 | B2 | 1/2012 | DeAngelis | |
| 8,580,290 | B2 * | 11/2013 | DeAngelis | C07H 5/04 424/423 |
| 8,980,608 | B2 * | 3/2015 | DeAngelis | A61K 31/726 435/193 |
| 2003/0017131 | A1 | 1/2003 | Park et al. | |
| 2003/0170883 | A1 * | 9/2003 | Martin | B01L 3/50855 435/288.4 |
| 2004/0087488 | A1 | 5/2004 | Parent et al. | |
| 2004/0197868 | A1 | 10/2004 | DeAngelis | |
| 2005/0255562 | A1 | 11/2005 | Rosenberg et al. | |
| 2005/0272696 | A1 | 12/2005 | DeAngelis | |
| 2006/0172967 | A1 | 8/2006 | Toida | |
| 2006/0188966 | A1 | 8/2006 | DeAngelis | |

(Continued)

FOREIGN PATENT DOCUMENTS

| | | |
|---|---|---|
| WO | WO 00/27437 | 5/2000 |
| WO | WO 01/80810 | 11/2001 |

(Continued)

OTHER PUBLICATIONS

May, B.J. et al. Complete genomic sequence of Pasteurella multocida, Pm70. Proc. Natl. Acad. Sci. (USA) Mar. 2001, vol. 98. No. 6, pp. 3460-3465.

Townsend, K.M. et al. Genetic organization of Pasteurella multocida cap loci and development of a multiplex capsular typing system. J. Clin. Microbiol. Mar. 2001. vol. 39. No. 3, pp. 924-929.

Hill, A.L., et al.: Identification of the *Xenopus laevis* cDNA for EXT1: A Phylogenetic Perspective. DNA Sequence, 2002 vol. 13 (2), pp. 85-92; ISSN: 10472-5179; Taylor & Francis, Ltd. (USA).

Rimler, R.B.: Presumptive Identification of *Pasteurella multocida serogroups* A, D and F by capsule depolymerisation with mucopolysaccharidases. Veterinary Record (1994) 134, 191-192 (USA).

(Continued)

*Primary Examiner* — Michael B Pallay

(74) *Attorney, Agent, or Firm* — Dunlap Codding, P.C.

(57) ABSTRACT

Biomaterial compositions that include an isolated heparosan polymer are disclosed, as well as kits containing such biomaterial compositions and methods of producing and using such biomaterial compositions.

12 Claims, 3 Drawing Sheets

(56) References Cited

U.S. PATENT DOCUMENTS

| | | | | |
|---|---|---|---|---|
| 2007/0128703 | A1 | 6/2007 | DeAngelis et al. | |
| 2008/0109236 | A1 | 5/2008 | DeAngelis et al. | |
| 2008/0226690 | A1 | 9/2008 | DeAngelis | |
| 2009/0136964 | A1 * | 5/2009 | Suzuki .................. | C07K 16/44 435/7.1 |
| 2010/0036001 | A1 | 2/2010 | DeAngelis | |
| 2012/0108802 | A1 | 5/2012 | DeAngelis et al. | |

FOREIGN PATENT DOCUMENTS

| | | | |
|---|---|---|---|
| WO | WO 02/89742 | 5/2002 | |
| WO | WO 03/029261 | 10/2003 | |
| WO | WO 2006106950 A1 * | 10/2006 | ............ C07K 16/44 |
| WO | WO 2009/014559 | 1/2009 | |
| WO | WO 2010/030342 | 3/2010 | |

OTHER PUBLICATIONS

Poggi A., et al.: Inhibition of B16-BL6 melanoma lung colonies by semisynthetic sulfaminoheparosan sulfates from *E. coli* K5 polysaccharide. Semin Thromb Hemost. Aug. 2002; 28(4): 383-92. vol. 28, No. 4.

Kim, B.T., et al.: Human tumor suppressor EXT gene family members EXTL1 and EXTL3 encode alpha 1,4-N-acetylglucosaminyltransferases that likely are involved in heparan sulfate/heparin biosynthesis. Proc. Natl. Acad. Sci. U.S.A. 2001 Jun. 19, 1998 (13):7176-81.

Vicenzi, E., et al.: Broad spectrum inhibition of HIV-1 infection by sulfated K5 *Escherichia coli* polysaccharide derivatives. AIDS. Jan. 24, 2003; 17 (2): 177-81; ISSN: 0269-9370 Lippincott Williams & Wilkins; Italy.

Lin, X, et al.: Expression and functional analysis of mouse EXT1, a homolog exostoses type 1 gene. Biochem Biophys Res Commun. Jul. 30, 1998; 248(3): 738-43; Academic Press.

Legeai-Mallet L., et al.: EXT 1 Gene Mutation Induces Chondrocyte Cytoskeletal Abnormalities and Defective Collagen Expression in the Exostoses. J Bone Miner Res. Aug. 2000; 15(8):1489-500.

McCormick, C., et al.: The putative tumor suppressor EXT1 alters the expression of cell-surface heparan sulfate. Nat. Genet. Jun. 1998; 19(2):158-61. (Canada).

Ahn, J., et al.: Cloning of the putative tumor suppressor gene for hereditary multiple exostoses (EXT1). Nat. Genet. Oct. 1995; 11(2):137-43.

Stickens, D., et al.: The EXT2 multiple exostoses gene defines a family of putative tumor suppressor genes. Nat. Genet. Sep. 1996; 14(1):25-32.

Simmons, A.D., et al.: A direct interaction between EXT proteins and glycosyltransferases is defective in hereditary multple exostoses. Hum. Mol. Genet. Nov. 1999; 8(12):2155-64. (USA).

Hagner-McWhirter A., et al.: Biosynthesis of heparin/heparan sulfate: kinetic studies of the glucuronyl C5-epimerase with N-sulfated derivatives of the *Escherichia coli* K5 capsular polysaccharide as substrates. Glycobiology. Feb. 2000; 10(2):159-71. Oxford University Press. (USA).

Lidholt, K., et al.: Biosynthesis of heparin. The D-glucuronosyl- and N-acetyl-D-glucosaminyltransferase reactions and their relation to polymer modification. Biochem J. Oct. 1, 1992;287 (pt 1):21-9 (Sweden).

Lin, X, et al.: Disruption of gastrulation and heparan sulfate biosynthesis in EXT1-Deficient Mice. Dev. Biol. Aug. 15, 2000; 224(2):299-311. Academic Press. (USA).

Van Hul, W., et al.: Identification of a Third EXT-like Gene (EXTL3) Belonging to the EXT Gene Family; Genomics. Jan. 15, 1998;47(2):230-7. Academic Press. (Belgium).

Nader, H.B., et al.: New insights on the specificity of heparin and haparan sulfate lyases from Flavobacterium heparinum revealed by the use of synthetic derivatives of K5 polysaccharide from *E. coli* and 2-O-desulfated heparin. Glycoconj J. Jun. 1999; 16(6):265-70. Kluwer Academic Publishers. Manufactured in the Netherlands. (Brazil).

Naggi, A., et al.: Toward a Biotechnological Heparin through Combined Chemical and Enzymatic Modification of the *Escherichia coli* K5 Polysaccharide. Seminars in Thrombosis and Hemostasis, vol. 27, No. 5, 2001; pp. 437-443. (Italy).

Leali, D., et al.: Fibroblast Growth Factor-2 Antagonist Activity and Angiostatic Capacity of Sulfated *Escherichia coli* K5 Polysaccharide Derivatives. The Journal of Biological Chemistry, vol. 276, No. 41. ISSN: Oct. 12, pp. 37900-37908, 2001. (Italy).

Duncan, G., et al.: The link between heparan sulfate and hereditary bone disease: finding a function for the EXT family of putative tumor suppressor proteins. The Journal of Clinical Investigation, Aug. 2001, vol. 108, No. 4, pp. 511-516. (USA).

Kim, B-T, et al.: Demonstration of a Novel Gene DEXT3 of *Drosophila melanogaster* as the Essential *N*-Acetylglucosamine Transferase in the Heparan Sulfate Biosynthesis. The Journal of Biological Chemistry, vol. 277, No. 16, ISSN: Apr. 19, pp. 13659-13665, 2002. (Sweden).

Sugahara, K., et al.: Heparin and Heparan Sulfate Biosynthesis. Life, 54:163-175, 2002. (Japan).

Lind, T., et al.: Biosynthesis of Heparin/Heparan Sulfate. The Journal of Biological Chemistry, vol. 268, No. 28, ISSN: Oct. 5, pp. 20705-20708, 1993. (Sweden).

Wei, G., et al.: Location of the Glucuronosyltransferase Domain in the Heparan Sulfate Copolymerase EXT1 by Analysis of Chinese Hamster Ovary Cell Mutants. The Journal of Biological Chemistry, vol. 275, No. 36, ISSN: Sep. 8, pp. 27733-27740, 2000. (USA).

Razi, N., et al.: Structural and functional properties of heparin analogues obtained by chemical sulphation of *Escherichia coli* K5 capsular polysaccharide. Biochem J. Jul. 15, 1995;309 (pt2):465-72. (Sweden).

Kusche, M., et al.: Biosynthesis of heparin. Use of *Escherichia coli* K5 capsular polysaccharide as a model substrate in enzymic polymer-modification reactions. Biochem J. Apr. 1, 1991;275 (pt1): 151-8. (Sweden).

Casu, B., et al.: Heparin-like compounds prepared by chemical modification of capsular polysaccharide from *E. coli*. Elsevier Science 1994; pp. 271-284. (Italy).

Vann, W.F., et al.: The Structure of the Capsular Polysaccharide (K5 Antigen) of Urinary-Tract-Infective *Escherichia coli* 010:K5:H4. Biochem J. 1981; 116; pp. 359-364. (Germany).

Toyoda, H., et al.: Structural Analysis of Glycosaminoglycans in *Drosophila* and *Caenorhabditis elegans* and Demonstrations That *tout-velu*, a *Drosophila* Gene Related to EXT Tumor Suppressors, Affects Heparan Sulfate in Vivo. The Journal of Biological Chemistry, vol. 275, No. 4; ISSN: Jan. 28, pp. 2269-2275, 2000. (Japan).

Zak, B.M., et al.: Hereditary multiple exostoses and heparan sulfate polymerization. Biochimica et Biophysica Acta 1573 (2002) 346-355. (USA).

Katada, T., et al.: cDNA cloning and distribution of XEXT1, the *Xenopus* homologue of EXT1. Dev Genese Evol. (2002) 212:248-250. (Japan).

Kitagawa, H., et al.: The Tumor Suppressor EXT-like Gene EXTL2 Encodes an 1, 4-N-Acety1hexosaminylatransferase That Transfers N-Acetylgalactosamine and N-Acetylglucosamine to the Common Clycosaminoglycan-Protein Linkage Region. The Journal of Biological Chemistry. 263(20):13933-139337.

Kitagawa, H., et al.: rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate. The Journal of Biological Chemistry, vol. 276, No. 7; ISSN: Feb. 16, pp. 4834-4838, 2001. (Japan).

Song, G., et al.: Identification of mutations in the human EXT1 and EXT2 genes. Chin J. Med. Genet., Aug. 1999, vol. 16. No. 4, pp. 208-210. (China).

Clines, G.A., et al.: The Structure of the Human Multiple *Exostoses 2* Gene and Characterization of Homologs in Mouse and *Caenorhabditis elegans*. Cold Spring Harbor Laboratory Press 1997; ISSN: 1057-9803, pp. 359-367. (USA).

(56) References Cited

OTHER PUBLICATIONS

Wise, C.A., et al.: Identification and Localization of the Gene for EXTL, a Third Member of the Multiple Exostoses Gene Family. Cold Spring Harbor Laboratory Press 1997; ISSN: 1057-9803, pp. 10-16. (USA).
Linhardt, R.J., et al.: Production and Chemical Processing of Low Molecular Weight Heparins. Thieme Medical Publishers, Inc. 1999, vol. 25, Suppl. 3, pp. 5-16. (USA).
Fareed, J.: Heparin, Its Fractions, Fragments and Derivatives. Some Newer Perspectives. Seminars in Thrombosis and Hemostasis, vol. 11, No. 1, 1985, pp. 1-9.
Lind, T., et al.: The Putative Tumor Suppressors EXT1 and EXT2 Are Glycosyltransferases Required for the Biosynthesis of Heparan Sulfate. The Journal of Biological Chemistry, vol. 273, No. 41, ISSN: Oct. 9, pp. 26265-26268, 1998. (Sweden).
Senay, C., et al.: The EXT1/EXT2 tumor suppressors: catalytic activities and role in heparan sulfate biosynthesis. EMBO Reports vol. 1, No. 3, pp. 282-286, 2000. ((Sweden).
Bio Tie Therapies; BioHeparin—Prospectus; Jun. 2001. (Finland).
Sasisekharan, R., et al.: Heparin and heparan sulfate: biosynthesis, structure and function. Elsevier Science, Ltd. 2000; 1367-5931; pp. 626-631. (USA).
Pedersen, L.C., et al.: Heparan/Chondroitin Sulfate Biosynthesis. The Journal of Biological Chemistry, vol. 275, No. 44; ISSN: Nov. 3, pp. 34580-34585, 2000. (USA).
Finke, A., et al.: Biosynthesis of the *Escherichia coli* K5 Polysaccharide, a Representative of Group II Polysaccharides: Polymerization In Vitro and Characterization of the Product. Journal of Bacteriology, Jul. 1999, pp. 4088-4094. (Germany).
Griffiths, G., et al.: Characterization of the Glycosyltransferase Enzyme from the *Escherichia coli* K5 Capsule Gene Cluster and Identification and Charaterization of the Glucuronyl Active Site. The Journal of Biological Chemistry, vol. 273, No. 19, ISSN: May 8, pp. 11752-11757, 1998. (United Kingdom).
Hodson, N., et al.: Identification That KfiA, a Protein Essential for the Biosynthesis of the *Escherichia coli* K5 Capsular Polysaccharide, Is a UDP-GlcNAc Glycosyltransferase. The Journal of Biological Chemistry, vol. 275, No. 35, ISSN: Sep. 1, pp. 27311-27315, 2000. (United Kingdom).
Boyce, J.D., et al.: *Pasteurella multocida* capsule: composition, function and genetics. Journal of Biotechnology 83 (2000) pp. 153-160. (Australia).
Rimler, R.B., et al.: Influence of chondroitinase on direct hemagglutnation titers and phagocytosis of *Pasteurella multocida* serogroups A, D and F. Veterinary Microbiology 47 (1995) pp. 287-294. (USA).
Rigg, G.P., et al.: The localization of KpsC, S and T, and KfiA, C and D Proteins Involved in the biosynthesis of the *Escherichia coli* K5 capsular polysaccharide: evidence for a membrane-bound complex. Microbiology (1998), 144, 2905-2914. (United Kingdom).
DeAngelis, P.L., et al.: Identification of the capsular polysaccharides of Type D and F *Pasteurella multocida* as unmodified heparin and chondroitin, respectively. Carbohydrate Research 337 (2002) pp. 1547-1552. (USA).
McCormick, C., et al.: The putative tumor suppressors EXT1 and EXT2 form a stable complex that accumulates in the Golgi apparatus and catalyzes the synthesis of heparan sulfate. PNAS, Jan. 18, 2000, vol. 97, No. 2, pp. 668-673. (Canada).
Cheung, P.K., et al.: Etiological Point Mutations in the Hereditary Multiple Exostoses Gene EXT1: A Functional Analysis of Heparan Sulfate Polymerase Activity. Am. J. Hum. Genet. 69:55-66, 2001. (Canada).
Wyatt Technology Corporation: Heparin Characterization. Apr. 5, 1997; www.tigc.org.
Soldani, G., et al.: Experimental and Clinical Pharmacology of Glycosaminoglycans (GAGs). Drugs Exptl. Clin. Res. XVII(1) 81-85 (1991). (Italy).
Van Aken, H., et al.: Anticoagulation: The Present and Future. Clin. Appl. Thrombosis/Hemostasis, 7(3): 195-204, 2001. (Germany).
Lidholt, K., et al.: Substrate specificities of glycosyltransferases involved in formation of heparin precursor and *E. coli* K5 capsular polysaccharides. Carbohydrate Research, 255 (1994) 87-101. (Sweden).
Roberts, I., et al.: Molecular Cloning and Analysis of Genes for Production of K5, K7, K12, and K92 Capsular Polysaccharides in *Escherichia coli*. J. Bacteriology; Dec. 1986, pp. 1228-1233. (Germany).
Kroncke, K.D., et al.: Expression of the *Escherichia coli* K5 Capsular Antigen: Immunoelectron Microscopic and Biochemical Studies with Recombinant *E. coli*. J. Bacteriology, Feb. 1990, pp. 1085-1091. (Germany).
Roberts, I.S., et al.: Common Organization of Gene Clusters for Production of Different Capsular Polysaccharides (K Antigens) in *Escherichia coli*. J. Bacteriology, Mar. 1988, pp. 1305-1310. (United Kingdom).
Petit, C., et al.: Region 2 of the *Escherichia coli* K5 capsule gene cluster encoding proteins for the biosynthesis of the K5 polysaccharide. Molecular Microbiology (1995) 17(4), pp. 611-620. (United Kingdom).
Smith, A.N., et al.: Molecular analysis of the *Escherichia coli* K5 *kps* locus: identification and characterization of an inner-membrane capsular polysaccharide transport system. Molecular Microbiology (1990) 4(11), pp. 1863-1869. (United Kingdom).
Bronner, D., et al.: Synthesis of the K5 (group II) capsular polysaccharide in transport-deficient recombinant *Escherichia coli*. FEMS Microbiology Letters 113 (1993), pp. 273-284. (Germany).
Pandit, K.K., et al.: Capsular hyaluronic acid in Pasteurella multocida type A and its counterpart in type D. Research in Veterinary Science. 54:20-24 (1993).
Linhardt, R.J. et al.; "Isolation and characterization of human heparin". Biochemistry, vol. 31(49): 12441-12445 (1992).
DeAngelis, P.; "Microbial glycosaminoglycan glycosyltransferases". Glysobiology, vol. 12(1): 9R-16R (2002).
Jing et al., Dissection of the two transferase activities of the *Pasteurella multocida* hyaluronan synthase: two active sites exist in one polypeptide, Glycobiology, vol. 10, pp. 883-890 (2000).
DeAngelis et al., "Identification and molecular cloning of a heparosan synthase from *Pasteurella multocida* type D", Journal of Biological Chemistry, pp. 1-23 (2001).
Peppas et al., "New Challenges in Biomaterials", Science, vol. 263:1715-1720 (1994).
Manzoni et al., "Production of K5 Polysaccharides of Different Molecular Weight by *Escherichia coli*", Journal of Bioactive and Compatible Polymers, vol. 11:301-311 (1996).
PCT Application No. PCT/US02/14581, Paul DeAngelis, International Search Report, dated Jun. 11, 2003.
PCT Application No. PCT/US02/14581, Paul DeAngelis, Written Opinion, dated Aug. 5, 2004.
U.S. Appl. No. 10/142,143, Paul DeAngelis, Requirement for Restriction/Election, dated Mar. 29, 2005.
U.S. Appl. No. 10/142,143, Paul DeAngelis, Response to Election, dated Apr. 29, 2005.
U.S. Appl. No. 10/142,143, Paul DeAngelis, Office Action, dated Oct. 28, 2005.
U.S. Appl. No. 10/142,143, Paul DeAngelis, Response to Office Action, dated Apr. 14, 2006.
U.S. Appl. No. 10/142,143, Paul DeAngelis, Office Action, dated Jun. 22, 2006.
U.S. Appl. No. 10/142,143, Paul DeAngelis, Response to Office Action, dated Dec. 22, 2006.
U.S. Appl. No. 10/142,143, Paul DeAngelis, Final Office Action, dated Apr. 5, 2007.
U.S. Appl. No. 10/142,143, Paul DeAngelis, Amendment Under 37 CRF 1.116, dated Jul. 3, 2007.
Australian Serial No. 2002256501, Paul DeAngelis, Examiner's First Report, dated Nov. 7, 2006.
Australian Serial No. 2002256501, Paul DeAngelis, Response to Examiner's First Report, dated Apr. 24, 2008.
EPO Application No. 02725971.2, Paul DeAngelis, Official Letter, dated Apr. 24, 2006.
EPO Application No. 02725971.2, Paul DeAngelis, Response to Official Letter, Nov. 3, 2006.

(56) References Cited

OTHER PUBLICATIONS

EPO Application No. 02725971.2, Paul DeAngelis, Official Letter, dated Mar. 2, 2009.
EPO Application No. 02725971.2, Paul DeAngelis, Response to Official Letter, dated Sep. 1, 2009.
EPO Application No. 02725971.2, Paul DeAngelis, Official Letter, dated Apr. 24, 2012.
PCT Application No. PCT/US08/04190, Paul DeAngelis, International Search Report & Written Opinion, dated Mar. 24, 2009.
PCT Application No. PCT/US09/05050, Paul DeAngelis, International Search Report & Written Opinion, dated Sep. 9, 2009.
U.S. Appl. No. 10/814,752, Paul DeAngelis, Requirement for Restriction/Election, dated Jul. 25, 2006.
U.S. Appl. No. 10/814,752, Paul DeAngelis, Amendment & Response to Election, dated Jan. 25, 2007.
U.S. Appl. No. 10/814,752, Paul DeAngelis, Office Action, dated Apr. 16, 2007.
U.S. Appl. No. 10/814,752, Paul DeAngelis, Amendment & Response to Office Action, dated Oct. 16, 2007.
U.S. Appl. No. 10/814,752, Paul DeAngelis, Office Action, dated Dec. 27, 2007.
U.S. Appl. No. 10/814,752, Paul DeAngelis, Amendment & Response to Office Action, dated Jun. 24, 2008.
U.S. Appl. No. 10/814,752, Paul DeAngelis, Final Office Action, dated Dec. 4, 2008.
U.S. Appl. No. 11/975,811, Paul DeAngelis, Requirement for Restriction/Election, dated Aug. 26, 2009.
U.S. Appl. No. 11/975,811, Paul DeAngelis, Amendment & Response to Election, dated Sep. 29, 2009.
U.S. Appl. No. 11/975,811, Paul DeAngelis, Office Action, dated Oct. 29, 2009.
U.S. Appl. No. 11/975,811, Paul DeAngelis, Amendment & Response to Office Action, dated Jan. 26, 2010.
U.S. Appl. No. 11/975,811, Paul DeAngelis, Notice of Allowance with Examiner's Amendment, dated Apr. 12, 2010.
U.S. Appl. No. 11/975,811, Paul DeAngelis, Amendment Under 37 CFR 1.312, dated Jun. 8, 2010.
U.S. Appl. No. 11/906,704, Paul DeAngelis, Requirement for Restriction/Election, dated Nov. 18, 2009.
U.S. Appl. No. 11/906,704, Paul DeAngelis, Amendment & Response to Election, dated Dec. 18, 2009.
U.S. Appl. No. 11/906,704, Paul DeAngelis, Requirement for Restriction/Election, dated Feb. 2, 2010.
U.S. Appl. No. 11/906,704, Paul DeAngelis, Amendment & Response to Election, dated Feb. 24, 2010.
U.S. Appl. No. 11/906,704, Paul DeAngelis, Office Action, dated May 17, 2010.
U.S. Appl. No. 11/906,704, Paul DeAngelis, Amendment & Response to Office Action, dated Nov. 17, 2010.
U.S. Appl. No. 11/906,704, Paul DeAngelis, Final Office Action, dated Jan. 18, 2011.
U.S. Appl. No. 11/906,704, Paul DeAngelis, Pre-Appeal Brief Request for Review, dated Jul. 18, 2011.
U.S. Appl. No. 11/906,704, Paul DeAngelis, Notice of Allowance with Examiner's Amendment, dated Aug. 31, 2011.
Australian Application No. 2008207616, Paul DeAngelis, Examiner's Report, dated Oct. 18, 2010.
Australian Application No. 2008207616, Paul DeAngelis, Response to Examiner's Report, dated Oct. 18, 2011.

* cited by examiner

SEQUENCE LISTING

```
<160> NUMBER OF SEQ ID NOS: 8

<210> SEQ ID NO 1
<211> LENGTH: 1851
<212> TYPE: DNA
<213> ORGANISM: Pasteurella multocida

<400> SEQUENCE: 1

atgagcttat ttaaacgtgc tactgagcta tttaagtcag gaaactataa agatgcacta      60

actctatatg aaaatatagc taaaatttat ggttcagaaa gccttgttaa atataatatt     120

gatatatgta aaaaaaatat aacacaatca aaaagtaata aaatagaaga agataatatt     180

tctggagaaa acaaattttc agtatcaata aaagatctat ataacgaaat aagcaatagt     240

gaattaggga ttacaaaaga aagactagga gcccccctc tagtcagtat tataatgact      300

tctcataata cagaaaaatt cattgaagcc tcaattaatt cactattatt gcaaacatac     360

aataacttag aagttatcgt tgtagatgat tatagcacag ataaaacatt tcagatcgca     420
```

-continued

```
tccagaatag caaactctac aagtaaagta aaaacattcc gattaaactc aaatctaggg    480

acatactttg cgaaaaatac aggaatttta aagtctaaag gagatattat tttctttcag    540

gatagcgatg atgtatgtca ccatgaaaga atcgaaagat gtgttaatgc attattatcg    600

aataaagata atatagctgt tagatgtgca tattctagaa taaatctaga aacacaaaat    660

ataataaaag ttaatgataa taaatacaaa ttaggattaa taactttagg cgtttataga    720

aaagtattta atgaaattgg tttttttaac tgcacaacca aagcatcgga tgatgaattt    780

tatcatagaa taattaaata ctatggtaaa aataggataa ataacttatt tctaccactg    840

tattataaca caatgcgtga agattcatta ttttctgata tggttgagtg ggtagatgaa    900

aataatataa agcaaaaaac ctctgatgct agacaaaatt atctccatga attccaaaaa    960

atacacaatg aaaggaaatt aaatgaatta aaagagattt ttagctttcc tagaattcat   1020

gacgccttac ctatatcaaa agaaatgagt aagctcagca accctaaaat tcctgtttat   1080

ataaatatat gctcaatacc ttcaagaata aaacaacttc aatacactat tggagtacta   1140

aaaaaccaat gcgatcattt tcatatttat cttgatggat atccagaagt acctgatttt   1200

ataaaaaaac tagggaataa agcgaccgtt attaattgtc aaaacaaaaa tgagtctatt   1260

agagataatg gaaagtttat tctattagaa aaacttataa aggaaaataa agatggatat   1320

tatataactt gtgatgatga tatccggtat cctgctgact acacaaacac tatgataaaa   1380

aaaattaata aatacaatga taaagcagca attggattac atggtgttat attcccaagt   1440

agagtcaaca agtatttttc atcagacaga attgtctata attttcaaaa acctttagaa   1500

aatgatactg ctgtaaatat attaggaact ggaactgttg cctttagagt atctattttt   1560

aataaatttt ctctatctga ttttgagcat cctggcatgg tagatatcta tttttctata   1620

ctatgtaaga aaaacaatat actccaagtt tgtatatcac gaccatcgaa ttggctaaca   1680

gaagataaca aaaacactga gaccttattt catgaattcc aaaatagaga tgaaatacaa   1740

agtaaactca ttatttcaaa caacccttgg ggatactcaa gtatatatcc actattaaat   1800

aataatgcta attattctga acttattccg tgtttatctt tttataacga g            1851


<210> SEQ ID NO 2
<211> LENGTH: 615
<212> TYPE: PRT
<213> ORGANISM: Pasteurella multocida

<400> SEQUENCE: 2

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125
```

-continued

```
Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270

Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540
```

-continued

```
Ile Leu Gln Val Cys Ile Ser Arg Pro Ser Asn Trp Leu Thr Glu Asp
545                 550                 555                 560

Asn Lys Asn Thr Glu Thr Leu Phe His Glu Phe Gln Asn Arg Asp Glu
                565                 570                 575

Ile Gln Ser Lys Leu Ile Ile Ser Asn Asn Pro Trp Gly Tyr Ser Ser
            580                 585                 590

Ile Tyr Pro Leu Leu Asn Asn Asn Ala Asn Tyr Ser Glu Leu Ile Pro
        595                 600                 605

Cys Leu Ser Phe Tyr Asn Glu
    610                 615


<210> SEQ ID NO 3
<211> LENGTH: 1940
<212> TYPE: DNA
<213> ORGANISM: Pasteurella multocida

<400> SEQUENCE: 3

aacaggggat aaggtcagta aatttaggat gatttttgac taatggataa atacttgaat      60

atccccatgg accgttttcc atgatcagct gagtttgttg ctcatcattg tctcgatatt     120

gatgatagag tgtttcgctg tctctattat cttccgttag ccagtttgct ggtcttgaaa     180

tacaaatctg aagaatatta tttttcttac acaagagaga gaaatagata tcagccatgc     240

ctgaatgggt aaagtcagaa agagaaaatt gattaaagag actgactcta aagctaacag     300

ttcctgtacc taatacattg accgctttgt ctttttccag aggtttatag aagctatata     360

ccagtctatc cgccgaaaaa tatttggtca ttctacttgg aaagagaatg ccgtgtaaac     420

caataaccgc tttatcatcg tattcattca gcttcttgat catcgtattg atgtaatcgc     480

ttggatagat aatgtcatca tcacaggtta tataatatcc atcttgattt ttttcaatca     540

actcttccag taaaatgaat ttgccattat ctctaatgga gttatcttta tctttgcaat     600

gaacaacggt tgctttatta cctaaatttt ttatgaagtc agggatttct acatagccat     660

caagataaat atgaaaatga tcacattgat tttttagtat gccgataata cgtcgtaatt     720

gcgctattct tgagggaata gaacaaatat tgatataaac aggaatctta ggattggaca     780

acttactcat ttcttgtggt actggtaagg catcgtaaat acgagggaat tgaaaaagat     840

ttttgaaatc atgtgaggca gtttcgttat gcatcgcttg aaacagggtt gcataatgtt     900

gtctggtatc agacattttc tgtattatgt tatgattgtc tatccattca accatatcag     960

taaataaaga gttttctctc attgtgttgt agtataacgg caagagtaaa tttttttattt    1020

tttcttttcc ataatatttc gcaattctat gaaaaaactc atcatctgag cctttagtcg    1080

tacaattgaa gaaaccaatt tcttgaaata cttttctgtg catacccaag gttataaaac    1140

ctaatctata atccatatta ttgactttaa tgatatgttg tgtttctggt gctagtcttg    1200

agtatgcaca acgaacagca atagtttctt tattagctaa taatatattt acacatcttt    1260

ctattctttc atgatgacat acatcatcac tatcttgaaa gaaaataatg tcacctttag    1320

attttaatat gcctgtattt ttcgcaaagt aagttcctag gtttgaattt aatctaaata    1380

ctctgacttt gcttgttgta ttcgctattc tcgaggcaat ttcaaatgta ttatccgagc    1440

tatcatcatc tacaataata atttctatgt ttttatatgt ttgtaacaat aatgaattaa    1500

tagaagcttc gataaattgc gctgtattgt gagatgtcat gataatactg actaatggat    1560

ttacgctgtt ggtttctttg actaacccta aatcactttt agcgacttca ttatataaat    1620

ctgttattga tgttgtttgc ttatcttttt ctagctttgc ttctaatgct tgattatagg    1680
```

-continued

```
tatatatttt ttcaaattct tgcagaacca attggagttg ttttaataaa agtttatttt   1740

cgttttcaag ggatgcggat agcggatgtt tactgtcctg ttttgccaat aaagtttgtt   1800

gagaaataat gtctttgttt aaagttgttt ttagactatc aattttattt tgaaaggtgt   1860

tgagttcatt ttctttttca tgttgggggg gatttttagt catttgtttt tgagtcatct   1920

cttttttttct cttcatttca                                              1940


<210> SEQ ID NO 4
<211> LENGTH: 651
<212> TYPE: PRT
<213> ORGANISM: Pasteurella multocida

<400> SEQUENCE: 4

Met Lys Arg Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Ala Ser Leu Glu
    50                  55                  60

Asn Glu Asn Lys Leu Leu Leu Lys Gln Leu Gln Leu Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Val Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Arg Lys Val Phe Gln Glu Ile Gly Phe Phe Asn Cys Thr Thr Lys
        275                 280                 285

Gly Ser Asp Asp Glu Phe Phe His Arg Ile Ala Lys Tyr Tyr Gly Lys
    290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
```

-continued

```
                325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
        355                 360                 365

Gln Phe Pro Arg Ile Tyr Asp Ala Leu Pro Val Pro Gln Glu Met Ser
    370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Arg Arg Ile Ile Gly Ile Leu Lys Asn
                405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
        435                 440                 445

Asp Lys Asp Asn Ser Ile Arg Asp Asn Gly Lys Phe Ile Leu Leu Glu
    450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
                485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
        515                 520                 525

Phe Tyr Lys Pro Leu Glu Lys Asp Lys Ala Val Asn Val Leu Gly Thr
    530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
                565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
        595                 600                 605

Asp Asn Asp Glu Gln Gln Thr Gln Leu Ile Met Glu Asn Gly Pro Trp
    610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
                645                 650


<210> SEQ ID NO 5
<211> LENGTH: 1854
<212> TYPE: DNA
<213> ORGANISM: Pasteurella multocida

<400> SEQUENCE: 5

atgagcttat ttaaacgtgc tactgagcta tttaagtcag gaaactataa agatgcacta      60

actctatatg aaaatatagc taaaatttat ggttcagaaa gccttgttaa atataatatt     120

gatatatgta aaaaaaatat aacacaatca aaaagtaata aaatagaaga agataatatt     180

tctggagaaa acaaattttc agtatcaata aaagatctat ataacgaaat aagcaatagt     240

gaattaggga ttacaaaaga aagactagga gcccccccctc tagtcagtat tataatgact     300
```

-continued

```
tctcataata cagaaaaatt cattgaagcc tcaattaatt cactattatt gcaaacatac    360
aataacttag aagttatcgt tgtagatgat tatagcacag ataaaacatt tcagatcgca    420
tccagaatag caaactctac aagtaaagta aaaacattcc gattaaactc aaatctaggg    480
acatactttg cgaaaaatac aggaatttta aagtctaaag gagatattat tttctttcag    540
gatagcgatg atgtatgtca ccatgaaaga atcgaaagat gtgttaatgc attattatcg    600
aataaagata atatagctgt tagatgtgca tattctagaa taaatctaga aacacaaaat    660
ataataaaag ttaatgataa taaatacaaa ttaggattaa taactttagg cgtttataga    720
aaagtattta atgaaattgg ttttttttaac tgcacaacca aagcatcgga tgatgaattt    780
tatcatagaa taattaaata ctatggtaaa aataggataa ataacttatt tctaccactg    840
tattataaca caatgcgtga agattcatta ttttctgata tggttgagtg ggtagatgaa    900
aataatataa agcaaaaaac ctctgatgct agacaaaatt atctccatga attccaaaaa    960
atacacaatg aaaggaaatt aaatgaatta aaagagattt ttagctttcc tagaattcat   1020
gacgccttac ctatatcaaa agaaatgagt aagctcagca accctaaaat tcctgtttat   1080
ataaatatat gctcaatacc ttcaagaata aaacaacttc aatacactat tggagtacta   1140
aaaaaccaat gcgatcattt tcatatttat cttgatggat atccagaagt acctgatttt   1200
ataaaaaaac tagggaataa agcgaccgtt attaattgtc aaaacaaaaa tgagtctatt   1260
agagataatg gaaagtttat tctattagaa aaacttataa aggaaaataa agatggatat   1320
tatataactt gtgatgatga tatccggtat cctgctgact acataaacac tatgataaaa   1380
aaaattaata aatacaatga taaagcagca attggattac atggtgttat attcccaagt   1440
agagtcaaca agtatttttc atcagacaga attgtctata attttcaaaa acctttagaa   1500
aatgatactg ctgtaaatat attaggaact ggaactgttg cctttagagt atctatttt   1560
aataaatttt ctctatctga ttttgagcat cctggcatgg tagatatcta tttttctata   1620
ctatgtaaga aaaacaatat actccaagtt tgtatatcac gaccatcgaa ttggctaaca   1680
gaagataaca aaaacactga gaccttattt catgaattcc aaaatagaga tgaaatacaa   1740
agtaaactca ttatttcaaa caacccttgg ggatactcaa gtatatatcc attattaaat   1800
aataatgcta attattctga acttattccg tgtttatctt tttataacga gtaa          1854
```

<210> SEQ ID NO 6
<211> LENGTH: 617
<212> TYPE: PRT
<213> ORGANISM: Pasteurella multocida

<400> SEQUENCE: 6

```
Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95
```

-continued

```
Ile Ile Met Thr Ser His Asn Thr Glu Lys Phe Ile Glu Ala Ser Ile
            100                 105                 110

Asn Ser Leu Leu Leu Gln Thr Tyr Asn Asn Leu Glu Val Ile Val Val
        115                 120                 125

Asp Asp Tyr Ser Thr Asp Lys Thr Phe Gln Ile Ala Ser Arg Ile Ala
    130                 135                 140

Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
```

```
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
                565                 570                 575

Asp Glu Ile Gln Ser Lys Leu Ile Ile Ser Asn Asn Pro Trp Gly Tyr
            580                 585                 590

Ser Ser Ile Tyr Pro Leu Leu Asn Asn Asn Ala Asn Tyr Ser Glu Leu
        595                 600                 605

Ile Pro Cys Leu Ser Phe Tyr Asn Glu
    610                 615


<210> SEQ ID NO 7
<211> LENGTH: 565
<212> TYPE: PRT
<213> ORGANISM: Pasteurella multocida

<400> SEQUENCE: 7

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
            100                 105                 110

Asn Ser Leu Leu Leu Gln Thr Tyr Asn Leu Glu Val Ile Val Val Asp
        115                 120                 125

Asp Tyr Ser Thr Asp Lys Thr Phe Gln Ile Ala Ser Arg Ile Ala Asn
    130                 135                 140

Ser Thr Ser Lys Val Lys Thr Phe Arg Leu Asn Ser Asn Leu Gly Thr
145                 150                 155                 160

Tyr Phe Ala Lys Asn Thr Gly Ile Leu Lys Ser Lys Gly Asp Ile Ile
                165                 170                 175

Phe Phe Gln Ser Asp Asp Val Cys His His Glu Arg Ile Glu Arg Cys
            180                 185                 190

Val Asn Ala Leu Leu Ser Asn Lys Asp Asn Ile Ala Val Arg Cys Ala
        195                 200                 205

Tyr Ser Arg Ile Asn Leu Glu Thr Gln Asn Ile Ile Lys Val Asn Asp
    210                 215                 220

Asn Lys Tyr Lys Leu Gly Leu Ile Thr Leu Gly Val Tyr Arg Lys Val
225                 230                 235                 240

Phe Asn Glu Ile Gly Phe Phe Asn Cys Thr Thr Lys Ala Ser Asp Asp
                245                 250                 255

Glu Phe Tyr His Arg Ile Ile Lys Tyr Tyr Gly Lys Asn Arg Ile Asn
            260                 265                 270
```

-continued

```
Asn Leu Phe Leu Pro Leu Tyr Tyr Asn Thr Met Arg Glu Asp Ser Leu
        275                 280                 285

Phe Ser Asp Met Val Glu Trp Val Asp Glu Asn Asn Ile Lys Gln Lys
    290                 295                 300

Thr Ser Asp Ala Arg Gln Asn Tyr Leu His Glu Phe Gln Lys Ile His
305                 310                 315                 320

Asn Glu Arg Lys Leu Asn Glu Leu Lys Glu Ile Phe Ser Phe Pro Arg
                325                 330                 335

Ile His Asp Ala Leu Pro Ile Ser Lys Glu Met Ser Lys Leu Ser Asn
            340                 345                 350

Pro Lys Ile Pro Val Tyr Ile Asn Ile Cys Ser Ile Pro Ser Arg Ile
        355                 360                 365

Lys Gln Leu Gln Tyr Thr Ile Gly Val Leu Lys Asn Gln Cys Asp His
    370                 375                 380

Phe His Ile Tyr Leu Asp Gly Tyr Pro Glu Val Pro Asp Phe Ile Lys
385                 390                 395                 400

Lys Leu Gly Asn Lys Ala Thr Val Ile Asn Cys Gln Asn Lys Asn Glu
                405                 410                 415

Ser Ile Arg Asp Asn Gly Lys Phe Ile Leu Leu Glu Lys Leu Ile Lys
            420                 425                 430

Glu Asn Lys Asp Gly Tyr Tyr Ile Thr Cys Asp Asp Asp Ile Arg Tyr
        435                 440                 445

Pro Ala Asp Tyr Thr Asn Thr Met Ile Lys Lys Ile Asn Lys Tyr Asn
    450                 455                 460

Asp Lys Ala Ala Ile Gly Leu His Gly Val Ile Phe Pro Ser Arg Val
465                 470                 475                 480

Asn Lys Tyr Phe Ser Ser Asp Arg Ile Val Tyr Asn Phe Gln Lys Pro
                485                 490                 495

Leu Glu Asn Asp Thr Ala Val Asn Ile Leu Gly Thr Gly Thr Val Ala
            500                 505                 510

Phe Arg Val Ser Ile Phe Asn Lys Phe Ser Leu Ser Asp Phe Glu His
        515                 520                 525

Pro Gly Met Val Asp Ile Tyr Phe Ser Ile Leu Cys Lys Lys Asn Asn
    530                 535                 540

Ile Leu Gln Val Cys Ile Ser Arg Pro Ser Asn Trp Leu Thr Glu Asp
545                 550                 555                 560

Asn Lys Asn Thr Glu
                565


<210> SEQ ID NO 8
<211> LENGTH: 538
<212> TYPE: PRT
<213> ORGANISM: Pasteurella multocida

<400> SEQUENCE: 8

Ser Asn Ser Glu Leu Gly Ile Thr Lys Glu Arg Leu Gly Ala Pro Pro
1               5                   10                  15

Leu Val Ser Ile Ile Met Thr Ser His Asn Thr Glu Lys Phe Ile Glu
            20                  25                  30

Ala Ser Ile Asn Ser Leu Leu Leu Gln Thr Tyr Asn Leu Glu Val Ile
        35                  40                  45

Val Val Asp Asp Tyr Ser Thr Asp Lys Thr Phe Gln Ile Ala Ser Arg
    50                  55                  60

Ile Ala Asn Ser Thr Ser Lys Val Lys Thr Phe Arg Leu Asn Ser Asn
65                  70                  75                  80
```

-continued

```
Leu Gly Thr Tyr Phe Ala Lys Asn Thr Gly Ile Leu Lys Ser Lys Gly
                85                  90                  95

Asp Ile Ile Phe Phe Gln Ser Asp Asp Val Cys His His Glu Arg Ile
            100                 105                 110

Glu Arg Cys Val Asn Ala Leu Leu Ser Asn Lys Asp Asn Ile Ala Val
        115                 120                 125

Arg Cys Ala Tyr Ser Arg Ile Asn Leu Glu Thr Gln Asn Ile Ile Lys
    130                 135                 140

Val Asn Asp Asn Lys Tyr Lys Leu Gly Leu Ile Thr Leu Gly Val Tyr
145                 150                 155                 160

Arg Lys Val Phe Asn Glu Ile Gly Phe Phe Asn Cys Thr Thr Lys Ala
                165                 170                 175

Ser Asp Asp Glu Phe Tyr His Arg Ile Ile Lys Tyr Tyr Gly Lys Asn
            180                 185                 190

Arg Ile Asn Asn Leu Phe Leu Pro Leu Tyr Tyr Asn Thr Met Arg Glu
        195                 200                 205

Asp Ser Leu Phe Ser Asp Met Val Glu Trp Val Asp Glu Asn Asn Ile
    210                 215                 220

Lys Gln Lys Thr Ser Asp Ala Arg Gln Asn Tyr Leu His Glu Phe Gln
225                 230                 235                 240

Lys Ile His Asn Glu Arg Lys Leu Asn Glu Leu Lys Glu Ile Phe Ser
                245                 250                 255

Phe Pro Arg Ile His Asp Ala Leu Pro Ile Ser Lys Glu Met Ser Lys
            260                 265                 270

Leu Ser Asn Pro Lys Ile Pro Val Tyr Ile Asn Ile Cys Ser Ile Pro
        275                 280                 285

Ser Arg Ile Lys Gln Leu Gln Tyr Thr Ile Gly Val Leu Lys Asn Gln
    290                 295                 300

Cys Asp His Phe His Ile Tyr Leu Asp Gly Tyr Pro Glu Val Pro Asp
305                 310                 315                 320

Phe Ile Lys Lys Leu Gly Asn Lys Ala Thr Val Ile Asn Cys Gln Asn
                325                 330                 335

Lys Asn Glu Ser Ile Arg Asp Asn Gly Lys Phe Ile Leu Leu Glu Lys
            340                 345                 350

Leu Ile Lys Glu Asn Lys Asp Gly Tyr Tyr Ile Thr Cys Asp Asp Asp
        355                 360                 365

Ile Arg Tyr Pro Ala Asp Tyr Thr Asn Thr Met Ile Lys Lys Ile Asn
    370                 375                 380

Lys Tyr Asn Asp Lys Ala Ala Ile Gly Leu His Gly Val Ile Phe Pro
385                 390                 395                 400

Ser Arg Val Asn Lys Tyr Phe Ser Ser Asp Arg Ile Val Tyr Asn Phe
                405                 410                 415

Gln Lys Pro Leu Glu Asn Asp Thr Ala Val Asn Ile Leu Gly Thr Gly
            420                 425                 430

Thr Val Ala Phe Arg Val Ser Ile Phe Asn Lys Phe Ser Leu Ser Asp
        435                 440                 445

Phe Glu His Pro Gly Met Val Asp Ile Tyr Phe Ser Ile Leu Cys Lys
    450                 455                 460

Lys Asn Asn Ile Leu Gln Val Cys Ile Ser Arg Pro Ser Asn Trp Leu
465                 470                 475                 480

Thr Glu Asp Asn Lys Asn Thr Glu Thr Leu Phe His Glu Phe Gln Asn
                485                 490                 495
```

-continued

| | | | | | | | | | | | | | | | |
|---|---|---|---|---|---|---|---|---|---|---|---|---|---|---|---|
| Arg | Asp | Glu | Ile | Gln | Ser | Lys | Leu | Ile | Ile | Ser | Asn | Asn | Pro | Trp | Gly |
| | | | 500 | | | | | 505 | | | | | 510 | | |
| Tyr | Ser | Ser | Ile | Tyr | Pro | Leu | Leu | Asn | Asn | Asn | Ala | Asn | Tyr | Ser | Glu |
| | | 515 | | | | | 520 | | | | | 525 | | | |
| Leu | Ile | Pro | Cys | Leu | Ser | Phe | Tyr | Asn | Glu | | | | | | |
| | 530 | | | | | 535 | | | | | | | | | |

HEPAROSAN-BASED BIOMATERIALS AND COATINGS AND METHODS OF PRODUCTION AND USE THEREOF

CROSS-REFERENCE TO RELATED APPLICATIONS/INCORPORATION BY REFERENCE STATEMENT

This application is a continuation of U.S. Ser. No. 12/080,060, filed Mar. 31, 2008; which claims benefit under 35 U.S.C. 119(e) of U.S. Ser. No. 60/921,296, filed Mar. 30, 2007. The ’060 application is also a continuation-in-part of U.S. Ser. No. 11/906,704, filed Oct. 3, 2007, now U.S. Pat. No. 8,088,604, issued Jan. 3, 2012; which claims benefit under 35 U.S.C. 119(e) of U.S. Ser. No. 60/849,034, filed Oct. 3, 2006.

The ’704 application Ser. No. 11/906,704 is also a continuation-in-part of U.S. Ser. No. 11/651,379, filed Jan. 9, 2007, now U.S. Pat. No. 7,579,173, issued Aug. 25, 2009; which is a continuation of U.S. Ser. No. 10/642,248, filed Aug. 15, 2003, now U.S. Pat. No. 7,223,571, issued May 29, 2007; which claims benefit under 35 U.S.C. 119(e) of provisional applications U.S. Ser. No. 60/404,356, filed Aug. 16, 2002; U.S. Ser. No. 60/479,432, filed Jun. 18, 2003; and U.S. Ser. No. 60/491,362, filed Jul. 31, 2003. The ’248 application is also a continuation-in-part of U.S. Ser. No. 10/195,908, filed Jul. 15, 2002, now abandoned; which is is a continuation-in-part of U.S. Ser. No. 10/142,143, filed May 8, 2002, now U.S. Pat. No. 7,307,159, issued Dec. 11, 2007; which claims benefit under 35 U.S.C. 119(e) of U.S. Ser. No. 60/289,554, filed May 8, 2001.

The contents of each of the above-referenced patents and patent applications are hereby expressly incorporated herein in their entirety by reference.

STATEMENT REGARDING FEDERALLY SPONSORED RESEARCH OR DEVELOPMENT

This invention was made with government support under National Research Grant Number C2163601 awarded by the National Science Foundation. The government has certain rights in the invention.

BACKGROUND

Polysaccharides are large carbohydrate molecules comprising from about 25 sugar units to thousands of sugar units. Oligosaccharides are smaller carbohydrate molecules comprising less than about 25 sugar units. Animals, plants, fungi and bacteria produce an enormous variety of polysaccharide structures that are involved in numerous important biological functions such as structural elements, energy storage, and cellular interaction mediation. Often, the polysaccharide’s biological function is due to the interaction of the polysaccharide with proteins such as receptors and growth factors. The glycosaminoglycan class of polysaccharides and oligosaccharides, which includes heparin, chondroitin, dermatan, keratan, and hyaluronic acid, plays major roles in determining cellular behavior (e.g., migration, adhesion) as well as the rate of cell proliferation in mammals. These polysaccharides and oligosaccharides are, therefore, essential for the correct formation and maintenance of the organs of the human body.

Several species of pathogenic bacteria and fungi also take advantage of the polysaccharide’s role in cellular communication. These pathogenic microbes form polysaccharide surface coatings or capsules that are identical or chemically similar to host molecules. For instance, Group A & C *Streptococcus* and Type A *Pasteurella multocida* produce authentic hyaluronic acid capsules, and other *Pasteurella multocida* (Type F and D) and pathogenic *Escherichia coli* (K4 and K5) are known to make capsules composed of polymers very similar to chondroitin and heparin. The pathogenic microbes form the polysaccharide surface coatings or capsules because such a coating is nonimmunogenic and protects the bacteria from host defenses, thereby providing the equivalent of molecular camouflage.

Enzymes alternatively called synthases, synthetases, or transferases, catalyze the polymerization of polysaccharides found in living organisms. Many of the known enzymes also polymerize activated sugar nucleotides. The most prevalent sugar donors contain UDP, but ADP, GDP, and CMP are also used depending on (1) the particular sugar to be transferred and (2) the organism. Many types of polysaccharides are found at, or outside of, the cell surface. Accordingly, most of the synthase activity is typically associated with either the plasma membrane on the cell periphery or the Golgi apparatus membranes that are involved in secretion. In general, these membrane-bound synthase proteins are difficult to manipulate by typical procedures, and only a few enzymes have been identified after biochemical purification.

A larger number of synthases have been cloned and sequenced at the nucleotide level using reverse genetic approaches in which the gene or the complementary DNA (cDNA) was obtained before the protein was characterized. Despite this sequence information, the molecular details concerning the three-dimensional native structures, the active sites, and the mechanisms of catalytic action of the polysaccharide synthases, in general, are very limited or absent. For example, the catalytic mechanism for glycogen synthesis is not yet known in detail even though the enzyme was discovered decades ago. In another example, it is still a matter of debate whether most of the enzymes that produce heteropolysaccharides utilize one UDP-sugar binding site to transfer both precursors, or alternatively, if there exists two dedicated regions for each substrate.

As stated above, polysaccharides are the most abundant biomaterials on earth, yet many of the molecular details of their biosynthesis and function are not generally well known. Hyaluronic acid or HA is a linear polysaccharide of the glycosaminoglycan class and is composed of up to thousands of β(1,4)GlcUA-β(1,3)GlcNAc repeats. In vertebrates, HA is a major structural element of the extracellular matrix and plays roles in adhesion and recognition. HA has a high negative charge density and numerous hydroxyl groups, therefore, the molecule assumes an extended and hydrated conformation in solution. The viscoelastic properties of cartilage and synovial fluid are, in part, the result of the physical properties of the HA polysaccharide. HA also interacts with proteins such as CD44, RHAMM, and fibrinogen thereby influencing many natural processes such as angiogenesis, cancer, cell motility, wound healing, and cell adhesion.

There are numerous medical applications of HA. For example, HA has been widely used as a viscoelastic replacement for the vitreous humor of the eye in ophthalmic surgery during implantation of intraocular lenses in cataract patients. HA injection directly into joints is also used to alleviate pain associated with arthritis. Chemically cross-linked gels and films are also utilized to prevent deleterious adhesions after abdominal surgery. Other researchers using other methods have demonstrated that adsorbed HA coatings also improve the biocompatibility of medical devices such as catheters and sensors by reducing fouling and tissue abrasion.

HA is also made by certain microbes that cause disease in humans and animals. Some bacterial pathogens, namely Gram-negative *Pasteurella multocida* Type A and Gram-positive *Streptococcus* Group A and C, produce an extracellular HA capsule which protects the microbes from host defenses such as phagocytosis. Mutant bacteria that do not produce HA capsules are $10^2$- and $10^3$-fold less virulent in comparison to the encapsulated strains. Furthermore, the *Paramecium bursaria Chlorella* virus (PBCV-1) directs the algal host cells to produce a HA surface coating early in infection.

The various HA synthases ("HAS"), the enzymes that polymerize HA, utilize UDP-GlcUA and UDP-GlcNAc sugar nucleotide precursors in the presence of a divalent Mn, Mg, or Co ion to polymerize long chains of HA. The HA chains can be quite large ($n=10^2$ to $10^4$). In particular, the HASs are membrane proteins localized to the lipid bilayer at the cell surface. During HA biosynthesis, the HA polymer is transported across the bilayer into the extracellular space. In all HASs, a single species of polypeptide catalyzes the transfer of two distinct sugars. In contrast, the vast majority of other known glycosyltransferases transfer only one monosaccharide.

Chondroitin is one of the most prevalent glycosaminoglycans (GAGS) in vertebrates as well as part of the capsular polymer of Type F *P. multocida*, a minor fowl cholera pathogen. This bacterium produces unsulfated chondroitin (16), but animals possess sulfated chondroitin polymers. The first chondroitin synthase from any source to be molecularly cloned was the *P. multocida* pmCS (DeAngelis and Padgett-McCue, 2000). The pmCS contains 965 amino acid residues and is about 90% identical to pmHAS. A soluble recombinant *Escherichia coli*-derived $pmCS^{1-704}$ catalyzes the repetitive addition of sugars from UDP-GalNAc and UDP-GlcUA to chondroitin oligosaccharide acceptors in vitro.

Heparosan [N-acetylheparosan], (-GlcUA-β1,4-GlcNAc-α1,4-), is the repeating sugar backbone of the polysaccharide found in the capsule of certain pathogenic bacteria as well as the biosynthetic precursor of heparin or heparan sulfate found in animals from hydra to vertebrates. In mammals, the sulfated forms bind to a variety of extremely important polypeptides including hemostasis factors (e.g., antithrombin III, thrombin), growth factors (e.g., EGF, VEGF), and chemokines (e.g., IL-8, platelet factor 4) as well as the adhesive proteins for viral pathogens (e.g., herpes, Dengue fever). Currently, heparin is extracted from animal tissue and used as an anticoagulant or antithrombotic drug. In the future, similar polymers and derivatives should also be useful for pharmacological intervention in a variety of pathologic conditions including neoplasia and viral infection.

Several enzyme systems have been identified that synthesize heparosan. In bacteria, either a pair of two separate glycosyltransferases (*Escherichia coli* KfiA and KfiC) or a single glycosyltransferase (*Pasteurella multocida* PmHS1 or PmHS2; (30, 47)) have been shown to polymerize heparosan; the enzymes from both species are homologous at the protein level. In vertebrates, a pair of enzymes, EXT 1 and EXT 2, that are not similar to the bacterial systems appear to be responsible for producing the repeating units of the polymer chain which is then subsequently modified by sulfation and epimerization.

The heparosan synthases from *P. multocida* possess both a hexosamine and a glucuronic acid transfer site in the same polypeptide chain, as shown by mutagenesis studies (Kane, T. A. et. al, J. Biol. Chem. 2006), and are therefore referred to as "dual-action" or bifunctional glycosyltransferases. These enzymes are complex because they employ both an inverting and a retaining mechanism when transferring the monosaccharide from UDP precursors to the non-reducing terminus of a growing chain. The two *Pasteurella* heparosan synthases, PmHS1 and PmHS2, are approximately 70% identical at the amino acid sequence level. The two genes are found in different regions of the bacterial chromosome: PmHS1 (hssA) is associated with the prototypical Gram-negative Type II carbohydrate biosynthesis gene locus but PmHS2 (hssB) resides far removed in an unspecialized region. As shown in the presently disclosed and claimed inventive concept(s), these catalysts have useful catalytic properties that may be harnessed by the hand of man.

Biomaterials (loosely defined as compounds or assemblies that are used to augment or substitute for components of natural tissues or body parts) are and will continue to be integral components of tissue engineering and regenerative medicine approaches. Complex procedures including transplants and stem cell therapies promise to enhance human health, but limited supplies of donor organs/tissues and the steep learning curves (as well as ethical debates) for pioneering approaches are obstacles. There is a growing demand for more routine applications of biomaterials, such as in reconstructive surgery, cosmetics, and medical devices. Therefore, there is a need in the art for new and improved biomaterials that may be used, for example but not by way of limitation, for dermal filler applications and for surface coatings for implanted devices.

Hyaluronan (HA), poly-L-lactic acid (poly[lactide]), calcium hydroxyapatite, and collagen based products dominate the current market for biomaterials utilized in reconstructive surgery and cosmetic procedures. However, these products have a number of undesirable properties for which manufacturers and healthcare professionals are seeking improvements. These disadvantages include, but are not limited to, limited lifetime, potential for immunogenicity and/or allergenicity, and non-natural appearance in aesthetic procedures. For enhancing biocompatibility and durability of an implanted device, HA, heparin, bovine serum albumin, pyrolytic carbon, or lipid coatings are employed to enhance biocompatibility of stents, catheters, and other implanted material devices. However, then products often cause fouling, clogging, or thrombus formation due to reactivity with the human body. Therefore, there is a need in the art for new and improved biomaterial compositions that overcome the disadvantages and defects of the prior art.

The presently claimed and disclosed inventive concept(s) overcomes the disadvantages and defects of the prior art. The presently claimed and disclosed inventive concept(s) is based on a biomaterial comprising heparosan, the natural biosynthetic precursor of heparin and heparan sulfate. This composition has numerous characteristics that provide improvements and advantages over existing products. While heparosan is very similar to HA and heparin, the molecule has greater stability within the body since it is not the natural final form of this sugar and therefore the body has no degradation enzymes or binding proteins that lead to loss of functionality. This property also reduces biofouling, infiltration, scarring and/or clotting. Heparosan is also more hydrophilic than synthetic coatings such as plastics or carbon. Finally, aside from bacterial HA, most other current filler biomaterials are typically animal-derived, which causes concern for side effects such as allergic reactions or stimulating granulation, and such side effects will not be a concern with the presently claimed and disclosed inventive concept(s).

DETAILED DESCRIPTION

Figure 1:
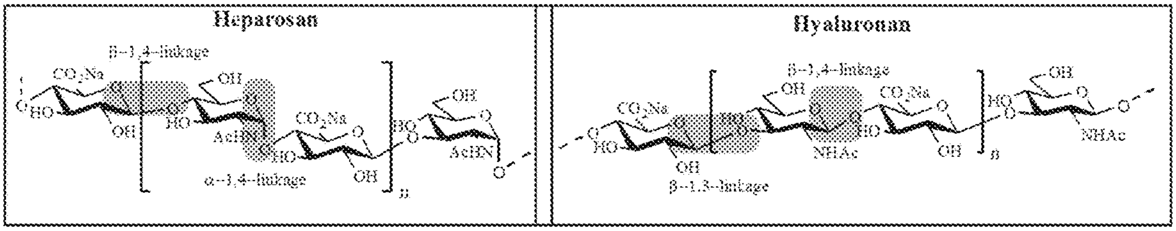
FIG. 1 schematically illustrates a comparison of heparosan and hyaluronan (HA) structures.

Before explaining at least one embodiment of the inventive concept(s) in detail by way of exemplary drawings, experimentation, results, and laboratory procedures, it is to be understood that the presently disclosed and claimed inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein in their entirety by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Glycosaminoglycans (GAGs) are linear polysaccharides composed of repeating disaccharide units containing a derivative of an amino sugar (either glucosamine or galactosamine). Hyaluronan [HA], chondroitin, and heparan sulfate/heparin contain a uronic acid as the other component of the disaccharide repeat while keratan contains a galactose. The GAGs are summarized in Table I.

TABLE I

| | | Post-Polymerization Modifications | |
|---|---|---|---|
| Polymer | Disaccharide Repeat | Vertebrates | Bacteria |
| Hyaluronan | β3GlcNAc β4GlcUA | None | None |
| Chondroitin | β3GalNAc β4GlcUA | O-sulfated/epimerized | None |
| Heparin/heparin | β4GlcNAc α4GlcUA | O,N-sulfated/epimerized | None |
| Keratan | β4GlcNAc β3Gal | O-sulfated | not reported |

An unnatural glycosaminoglycan (unnatural GAG) would be a composition of matter not normally found in known living vertebrates, animals or microbes; different arrangements or structures of chemical groups are added by the hand of man.

Vertebrates may contain all four types of GAGs, but the polysaccharide chain is often further modified after sugar polymerization. One or more modifications including O-sulfation of certain hydroxyls, deacetylation and subsequent N-sulfation, or epimerization of glucuronic acid to iduronic acid are found in most GAGs except HA. An amazing variety of distinct structures have been reported for chondroitin sulfate and heparan sulfate/heparin even within a single polymer chain. A few clever pathogenic microbes also produce unmodified GAG chains; the bacteria use extracellular polysaccharide coatings as molecular camouflage to avoid host defenses. The chondroitin and heparan sulfate/heparin chains in vertebrates are initially synthesized by elongation of a xylose-containing linkage tetrasaccharide attached to a variety of proteins. Keratan is either O-linked or N-linked to certain proteins depending on the particular molecule. HA and all of the known bacterial GAGs are not part of the classification of proteins known as glycoproteins. All GAGs except HA are found covalently linked to a core protein, and such combination is referred to as a proteoglycan. Glycoproteins are usually much smaller than proteoglycans and only contain from 1-60% carbohydrate by weight in the form of numerous relatively short, branched oligosaccharide chains, whereas a proteoglycan can contain as much as 95% carbohydrate by weight. The core protein in a proteoglycan is also usually a glycoprotein, therefore usually contains other oligosaccharide chains besides the GAGs.

GAGs and their derivatives are currently used in the medical field as ophthalmic and viscoelastic supplements, adhesion surgical aids to prevent post-operative adhesions, catheter and device coatings, and anticoagulants. Other current or promising future applications include anti-cancer medications, tissue engineering matrices, immune and neural cell modulators, anti-virals, proliferation modulators, and drug targeting agents.

Complex carbohydrates, such as GAGs, are information rich molecules. A major purpose of the sugars that make up GAGs is to allow communication between cells and extracellular components of multicellular organisms. Typically, certain proteins bind to particular sugar chains in a very selective fashion. A protein may simply adhere to the sugar, but quite often the protein's intrinsic activity may be altered and/or the protein transmits a signal to the cell to modulate its behavior. For example, in the blood coagulation cascade, heparin binding to inhibitory proteins helps shuts down the clotting response. In another case, HA binds to cells via the CD44 receptor that stimulates the cells to migrate and to proliferate. Even though long GAG polymers (i.e., $>10^2$ Da) are found naturally in the body, typically the protein's binding site interacts with a stretch of 4 to 10 monosaccharides. Therefore, oligosaccharides can be used to either (a) substitute for the polymer, or (b) to inhibit the polymer's action depending on the particular system.

HA polysaccharide plays structural roles in the eye, skin, and joint synovium. Large HA polymers ($\sim10^6$ Da) also stimulate cell motility and proliferation. On the other hand, shorter HA polymers ($\sim10^4$ Da) often have the opposite effect. HA-oligosaccharides composed of 10 to 14 sugars [$HA_{10-14}$] have promise for inhibition of cancer cell growth and metastasis. In an in vivo assay, mice injected with various invasive and virulent tumor cell lines (melanoma, glioma, carcinomas from lung, breast and ovary) develop a number of large tumors and die within weeks. Treatment with HA oligosaccharides greatly reduced the number and the size of tumors. Metastasis, the escape of cancer cells throughout the body, is one of the biggest fears of both the ailing patient and the physician. HA or HA-like oligosaccharides appear to serve as a supplemental treatment to inhibit cancer growth and metatasis.

The preliminary mode of action of the HA-oligosaccharide sugars is thought to be mediated by binding or interacting with one of several important HA-binding proteins (probably CD44 or RHAM) in the mammalian body. One proposed scenario for the anticancer action of HA-oligosaccharides is that multiple CD44 protein molecules in a cancer cell can bind simultaneously to a long HA polymer. This multivalent HA binding causes CD44 activation (perhaps mediated by dimerization or a receptor patching event) that triggers cancer cell activation and migration. However, if the cancer cell is flooded with small HA-oligosaccharides, then each CD44 molecule individually binds a different HA molecule in a monovalent manner such that no dimerization/patching event occurs. Thus no activation signal is transmitted to the cell. Currently, it is believed that the optimal HA-sugar size is 10 to 14 sugars. Although this size may be based more upon the size of HA currently available for testing rather than biological functionality—i.e., now that HA molecules and HA-like derivatives <10 sugars are available according to the methodologies of the present inventive concept(s), the optimal HA size or oligosaccharide composition may be found to be different.

It has also been shown that treatment with certain anti-CD44 antibodies or CD44-antisense nucleic acid prevents the growth and metastasis of cancer cells in a fashion similar to HA-oligosaccharides; in comparison to the sugars, however, these protein-based and nucleic acid-based reagents are somewhat difficult to deliver in the body and/or may have long-term negative effects. A very desirable attribute of HA-oligosaccharides for therapeutics is that these sugar molecules are natural by-products that can occur in small amounts in the healthy human body during the degradation of HA polymer; no untoward innate toxicity, antigenicity, or allergenic concerns are obvious.

Other emerging areas for the potential therapeutic use of HA oligosaccharides are the stimulation of blood vessel formation and the stimulation of dendritic cell maturation. Enhancement of wound-healing and resupplying cardiac oxygenation may be additional applications that harness the ability of HA oligosaccharides to cause endothelial cells to form tubes and sprout new vessels. Dendritic cells possess adjuvant activity in stimulating specific CD4 and CD8 T cell responses. Therefore, dendritic cells are targets in vaccine development strategies for the prevention and treatment of infections, allograft reactions, allergic and autoimmune diseases, and cancer.

Heparin interacts with many proteins in the body, but two extremely interesting classes are coagulation cascade proteins and growth factors. Antithrombin III [ATIII] and certain other hemostasis proteins are 100,000-fold more potent inhibitors of blood clotting when complexed with heparin. Indeed, heparin is so potent it must be used in a hospital setting and requires careful monitoring in order to avoid hemorrhage. Newer, processed lower molecular weight forms of heparin are safer, but this material is still a complex mixture. It has been shown that a particular pentasaccharide (5 sugars long) found in heparin is responsible for the ATIII-anticoagulant effect. But since heparin is a very heterogeneous polymer, it is difficult to isolate the pentasaccharide (5 sugars long) in a pure state. The pentasaccharide can also be prepared in a conventional chemical synthesis involving ~50 to 60 steps. However, altering the synthesis or preparing an assortment of analogs in parallel is not always feasible—either chemically or financially.

Many growth factors, including VEGF (vascular endothelial growth factor), HBEGF (heparin-binding epidermal growth factor), and FGF (fibroblast growth factor), bind to cells by interacting simultaneously with the growth factor receptor and a cell-surface heparin proteoglycan; without the heparin moiety, the potency of the growth factor plummets. Cell proliferation is modulated in part by heparin; therefore, diseases such as cancer and atherosclerosis are potential targets. Abnormal or unwanted proliferation would be curtailed if the growth factor was prevented from stimulating target disease-state cells by interacting with a heparin-like oligosaccharide analog instead of a surface-bound receptor. Alternatively, in certain cases, the heparin oligosaccharides alone have been shown to have stimulatory effects.

Chondroitin is the most abundant GAG in the human body, but all of its specific biological roles are not yet clear. Phenomenon such as neural cell outgrowth appears to be modulated by chondroitin. Both stimulatory and inhibitory effects have been noted depending on the chondroitin form and the cell type. Therefore, chondroitin or similar molecules are of utility in re-wiring synaptic connections after degenerative diseases (e.g., Alzheimer's) or paralytic trauma. The epimerized form of chondroitin (GlcUA converted to the C5 isomer, iduronic acid or IdoUA), dermatan, selectively inhibits certain coagulation proteins such as heparin cofactor II. By modulating this protein in the coagulation pathway instead of ATIII, dermatan appears to allow for a larger safety margin than heparin treatment for reduction of thrombi or clots that provoke strokes and heart attacks.

In the patent applications referenced and incorporated herein, several practical catalysts from *Pasteurella* bacteria that allow for the synthesis of the three most important human GAGs (i.e., the three known acidic GAGs) are described and enabled (e.g. HA, chondroitin, and heparin).

All of the known HA, chondroitin and heparosan/heparan sulfate/heparin glycosyltransferase enzymes that synthesize the alternating sugar repeat backbones in microbes and in vertebrates utilize UDP-sugar precursors and divalent metal cofactors (e.g., magnesium, cobalt, and/or manganese ion) near neutral pH according to the overall reaction:

$$nUDP\text{-}GlcUA + nUDP\text{-}HexNAc \rightarrow 2nUDP + [GlcUA\text{-}HexNAc]_n$$

where HexNAc=GlcNAc or GalNAc. Depending on the specific GAG and the particular organism or tissue examined, and the degree of polymerization, n, ranges from about 25 to about 10,000. Smaller molecules may be made in vitro, as desired. If the GAG is polymerized by a single polypeptide, the enzyme is called a synthase or co-polymerase.

As outlined in and incorporated by reference in the "Cross-Reference" section of this application hereinabove, the inventor has previously discovered four new dual-action enzyme catalysts from distinct isolates of the Gram-negative bacterium *Pasteurella multocida* using various molecular biology strategies. *P. multocida* infects fowl, swine, and cattle as well as many wildlife species. The enzymes are: a HA synthase, or PmHAS (see U.S. Ser. No. 10/217,613, filed Aug. 12, 2002, the entire contents of which are expressly incorporated herein by reference); a chondroitin synthase, or PmCS (see U.S. Ser. No. 09/842,484, filed Apr. 25, 2002, the entire contents of which are expressly incorporated herein by reference); and two heparosan synthases, or PmHS1 and PmHS2 (see U.S. Ser. No. 10/142,143, filed May 8, 2002, the entire contents of which are expressly incorporated herein by reference).

Most membrane proteins are relatively difficult to study due to their insolubility in aqueous solution, and the native HSs are no exception. However, the inventor has demonstrated in the prior application, incorporated herein above, that full-length, native sequence PmHS1 or PmHS2 can be converted into higher yield, soluble proteins that are purifiable by the addition of fusion protein partners, such as, but not limited to, maltose-binding protein (MBP).

The present inventive concept(s) encompasses methods of producing a variety of unique biocompatible molecules and coatings based on polysaccharides. Polysaccharides, especially those of the glycosaminoglycan class, serve numerous roles in the body as structural elements and signaling molecules. The biomaterial compositions of the presently disclosed and claimed inventive concept(s) may be utilized, for example but not by way of limitation, for augmenting tissues and for coating surfaces of implants. The polysaccharide coatings of the present inventive concept(s) are useful for integrating a foreign object within a surrounding tissue matrix. For example, a device's artificial components could be masked by the biocompatible coating to reduce immunoreactivity or inflammation.

The present inventive concept(s) is related to a biomaterial composition that includes an isolated heparosan polymer. The isolated heparosan polymer is biocompatible with a mammalian patient and is represented by the structure $(\text{-GlcUA-beta1,4-GlcNAc-alpha-1,4-})_n$, wherein n is a positive integer greater than or equal to 1. In one embodiment, n may be greater than 10, while in other embodiments, n may be about 1,000. The biomaterial composition is substantially not susceptible to hyaluronidases and thereby is not substantially degraded in vivo. In addition, the biomaterial composition may be recombinantly produced as described in detail herein, or the biomaterial composition may be isolated and purified from natural sources by any isolation/purification methods known in the art.

The heparosan polymer of the biomaterial composition may be linear or cross-linked. The biomaterial composition of the presently disclosed and claimed inventive concept(s) may be administered to a patient by any means known in the art; for example, but not by way of limitation, the biomaterial composition may be injectable and/or implantable. In addition, the biomaterial composition may be in a gel or semi-solid state, a suspension of particles, or the biomaterial composition may be in a liquid form.

Alternatively, the heparosan polymer of the biomaterial composition may be attached to a substrate. When attached to a substrate, the isolated heparosan polymer may be covalently (via a chemical bond) or non-covalently (via weak bonds) attached to the substrate. Examples of substrates that may be utilized in accordance with the presently disclosed and claimed inventive concept(s) include, but are not limited to, silica, silicon, semiconductors, glass, polymers, organic compounds, inorganic compounds, metals and combinations thereof. When the substrate is a metal, the metal may include, but is not limited to, gold, copper, stainless steel, nickel, aluminum, titanium, thermosensitive alloys and combinations thereof.

The presently disclosed and claimed inventive concept(s) also comprises biomaterial compositions comprising a cross-linked gel comprising isolated heparosan and at least one cross-linking agent. The cross-linking agent may be any cross-linking agent known in the art; specific examples of cross-linking agents that may be utilized in accordance with the presently disclosed and claimed inventive concept(s) include, but are not limited to, aldehydes, epoxides, polyaziridyl compounds, glycidyl ethers, divinyl sulfones, and combinations and derivatives thereof.

Any of the biomaterial compositions of the presently disclosed and claimed inventive concept(s) may be a moisturizing biomaterial that protects from dehydration; alternatively, any of the biomaterial compositions of the presently disclosed and claimed inventive concept(s) may be a lubricating biomaterial.

Another aspect of the presently disclosed and claimed inventive concept(s) is related to kits for in vivo administration of the biomaterial compositions described herein above to a mammalian patient.

The presently disclosed and claimed inventive concept(s) also relates to methods for providing a coating on a surface of a synthetic implant. In such methods, a synthetic implant and the biomaterial composition described herein above are provided. The biomaterial composition is disposed onto at least a portion of the surface of the synthetic implant and allowed to form a coating on the surface of the implant.

The presently disclosed and claimed inventive concept(s) is also related to methods of augmenting tissue in a patient. In such methods, the biomaterial composition described herein above is provided, and an effective amount thereof is administered to the mammalian patient. The biomaterial composition may be administered to the patient by any method known in the art, such as but not limited to, injection and/or implantation. When injected, the biomaterial composition may be in a liquid state or a suspension of particles, whereas when implanted, the biomaterial composition may be in a gel or semi-solid state, or may be attached to a substrate.

The presently disclosed and claimed inventive concept(s) also comprises biomaterial compositions comprising a cross-linked gel comprising isolated heparosan and at least one cross-linking agent. The cross-linking agent may be any cross-linking agent known in the art; specific examples of cross-linking agents that may be utilized in accordance with the presently disclosed and claimed inventive concept(s) include, but are not limited to, aldehydes, epoxides, polyaziridyl compounds, glycidyl ethers, divinyl sulfones, and combinations and derivatives thereof.

The presently disclosed and claimed inventive concept(s) also relates to methods of repairing voids in tissues of mammals, comprising injecting/implanting the biomaterial composition described herein above into said voids.

The presently disclosed and claimed inventive concept(s) also relates to methods of creating voids or viscus in tissues of mammals, comprising injecting/implanting the biomaterial composition described herein above into a tissue or a tissue engineering construct to create said voids or viscus.

The presently disclosed and claimed inventive concept(s) also relates to methods of reparative surgery or plastic surgery, comprising using the biomaterial compositions described herein above as filling material.

The presently disclosed and claimed inventive concept(s) further relates to methods of dermal augmentation and/or treatment of skin deficiency in a mammal, comprising injecting and/or implanting a biomaterial composition as described herein above into said mammal. The biomaterial composition is biocompatible, swellable, hydrophilic and substantially non-toxic, and the biomaterial composition swells upon contact with physiological fluids at the injection/implantation site.

The dermal augmentation method of the presently disclosed and claimed inventive concept(s) is especially suitable for the treatment of skin contour deficiencies, which are often caused by aging, environmental exposure, weight loss, child bearing, injury, surgery, in addition to diseases such as acne and cancer. Suitable for the treatment by the method of the presently disclosed and claimed inventive concept(s) are contour deficiencies such as frown lines, worry lines, wrinkles, crow's feet, marionette lines, stretch marks, and internal and external scars resulted from injury, wound, bite, surgery, or accident.

"Dermal augmentation" in the context of the presently disclosed and claimed inventive concept(s) refers to any change of the natural state of a mammal's skin and related areas due to external acts. The areas that may be changed by dermal augmentation include, but not limited to, epidermis, dermis, subcutaneous layer, fat, arrector pill muscle, hair shaft, sweat pore, and sebaceous gland.

In addition, the presently disclosed and claimed inventive concept(s) also relates to methods of medical or prophylactic treatment of a mammal, wherein such methods comprise administration of the biomaterial compositions described herein to a mammal in need of such a treatment.

Further, the presently disclosed and claimed inventive concept(s) also relates to methods of treatment or prophylaxis of tissue augmentation in a mammal, comprising administering a medical or prophylactic composition comprising a polysaccharide gel composition comprising the biomaterial composition described herein.

The presently disclosed and claimed inventive concept(s) is further related to a delivery system for a substance having biological or pharmacological activity, said system comprising a molecular cage formed of a cross-linked gel of heparosan or a mixed cross-linked gel of heparosan and at least one other hydrophilic polymer co-polymerizable therewith and having dispersed therein a substance having biological or pharmacological activity and which is capable of being diffused therefrom in a controlled manner.

The biomaterials of the presently disclosed and claimed inventive concept(s) may be utilized in any methods of utilizing biomaterials known in the art. For example but not by way of limitation, the biomaterial compositions of the presently disclosed and claimed inventive concept(s) may be utilized in any of the methods of utilizing other known biomaterials that are described in U.S. Pat. No. 4,582,865, issued to Balazs et al. on Apr. 15, 1986; U.S. Pat. No. 4,636,524, issued to Balazs et al. on Jan. 13, 1987; U.S. Pat. No. 4,713,448, issued to Balazs et al. on Dec. 15, 1987; U.S. Pat. No. 5,137,875, issued to Tsununaga et al. on Aug. 11, 1992; U.S. Pat. No. 5,827,937, issued to Ang on Oct. 27, 1998; U.S. Pat. No. 6,436,424, issued to Vogel et al. on Aug. 20, 2002; U.S. Pat. No. 6,685,963, issued to Taupin et al. on Feb. 3, 2004; and U.S. Pat. No. 7,060,287, issued to Hubbard et al. on Jun. 13, 2006. The entire contents of such patents are hereby expressly incorporated herein by reference, and therefore any of the methods described therein, when utilized with the novel biomaterial compositions of the presently claimed and disclosed inventive concept(s), also fall within the scope of the presently disclosed and claimed inventive concept(s).

Other specific examples of uses for the biomaterial compositions of the presently disclosed and claimed inventive concept(s) include, but are not limited to, (a) a persistent lubricating coating on a surface, such as but not limited to, surgical devices; (b) a long lasting moisturizer; (c) a viscoelastic supplement for joint maladies; and (d) a non-thrombotic, non-occluding blood conduit (such as but not limited to, a stent or artificial vessel, etc.). In addition, the biomaterial compositions of the presently disclosed and claimed inventive concept(s) may be utilized in tissue engineering to form a viscus or vessel duct or lumen by using the biomaterial compositions of the presently disclosed and claimed inventive concept(s) as a three-dimensional space maker; in this instance, the surrounding cells will not bind to the biomaterial compositions of the presently disclosed and claimed inventive concept(s), thereby making such biomaterial compositions well suited for this technology.

In addition, the presently disclosed and claimed inventive concept(s) further includes methods of doing business by producing the glycosaminoglycan polymers by the methods described herein above and selling and delivering such glycosaminoglycan polymers to a customer or providing such glycosaminoglycan polymers to a patient.

As used herein, the term "heparosan" will be understood to refer to the natural biosynthetic precursor of heparin and heparin sulfate. The sugar polymer heparosan is an unsulfated, unepimerized heparin molecule, and may also be referred to as "N-acetyl heparosan".

The term "tissue" as used herein will be understood to refer to a grouping of cells within an organism that are similarly characterised by their structure and function.

The term "biomaterial" as used herein will be understood to refer to any nondrug material that can be used to treat, enhance, protect, or replace any tissue, organ, or function in an organism. The term "biomaterial" also refers to biologically derived material that is used for its structural rather than its biological properties, for example but not by way of limitation, to the use of collagen, the protein found in bone and connective tissues, as a cosmetic ingredient, or to the use of carbohydrates modified with biotechnological processes as lubricants for biomedical applications or as bulking agents in food manufacture. A "biomaterial" is any material, natural or man-made, that comprises whole or part of a living structure or biomedical device which performs, auguments, protects, or replaces a natural function and that is compatible with the body.

As used herein, when the term "isolated" is used in reference to a molecule, the term means that the molecule has been removed from its native environment. For example, a polynucleotide or a polypeptide naturally present in a living animal is not "isolated", but the same polynucleotide or polypeptide separated from the coexisting materials of its natural state is "isolated". Further, recombinant DNA molecules contained in a vector are considered isolated for the purposes of the presently disclosed and claimed inventive concept(s). Isolated RNA molecules include in vivo or in vitro RNA replication products of DNA and RNA molecules. Isolated nucleic acid molecules further include synthetically produced molecules. Additionally, vector molecules contained in recombinant host cells are also isolated. Overall, this also applies to carbohydrates in general. Thus, not all "isolated" molecules need be "purified".

As used herein, when the term "purified" is used in reference to a molecule, it means that the concentration of the molecule being purified has been increased relative to molecules associated with it in its natural environment. Naturally associated molecules include proteins, nucleic acids, lipids and sugars but generally do not include water, buffers, and reagents added to maintain the integrity or facilitate the purification of the molecule being purified.

As used herein, the term "substantially purified" refers to a compound that is removed from its natural environment and is at least 60% free, preferably 75% free, and most preferably 90% free from other components with which it is naturally associated.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, such as more than about 85%, 90%, 95%, and 99%. In one embodiment, the object species is purified to essential homogeneity (contaminant species cannot be detected in the composition by conventional detection methods) wherein the composition consists essentially of a single macromolecular species.

As used herein, the term "substrate" will be understood to refer to any surface of which a coating may be disposed. Examples of substrates that may be utilized in accordance with the presently disclosed and claimed inventive concept(s) include, but are not limited to, silica, silicon, glass, polymers, organic compounds, inorganic compounds, metals and combinations thereof. When the substrate is a metal, the metal may include, but is not limited to, gold, copper, stainless steel, nickel, aluminum, titanium, thermosensitive alloys and combinations thereof.

The terms "gel" and "semi-solid" are used interchangeably herein and will be understood to include a colloidal system, with the semblance of a solid, in which a solid is dispersed in a liquid; the compound may have a finite yield stress. The term "gel" also refers to a jelly like material formed by the coagulation of a colloidal liquid. Many gels have a fibrous matrix and fluid filled interstices: gels are viscoelastic rather than simply viscous and can resist some mechanical stress without deformation. When pressure is applied to gels or semi-solids, they conform to the shape at which the pressure is applied.

The term "hydrogel" is utilized herein to describe a network of polymer chains that are water-insoluble, sometimes found as a colloidal gel in which water is the dispersion medium. Hydrogels are very absorbent natural or synthetic polymers, and may contain over 99% water. Hydrogels also possess a degree of flexibility very similar to natural tissue, due to their significant water content.

In addition, peptides and/or larger biologically active substances can be enclosed in hydrogels, thereby forming a sustained release composition.

As used herein, the term "effective amount" refers to an amount of a biomaterial composition or conjugate or derivative thereof sufficient to exhibit a detectable therapeutic or prophylactic effect without undue adverse side effects (such as toxicity, irritation and allergic response) commensurate with a reasonable benefit/risk ratio when used in the manner of the presently disclosed and claimed inventive concept(s). The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "substantially monodisperse in size" as used herein will be understood to refer to defined glycoasminoglycan polymers that have a very narrow size distribution. For example, substantially monodisperse glycosaminoglycan polymers having a molecular weight in a range of from about 3.5 kDa to about 0.5 MDa will have a polydispersity value (i.e., Mw/Mn, where Mw is the average molecular weight and Mn is the number average molecular weight) in a range of from about 1.0 to about 1.1, and preferably in a range from about 1.0 to about 1.05. In yet another example, substantially monodisperse glycosaminoglycan polymers having a molecular weight in a range of from about 0.5 MDa to about 4.5 MDa will have a polydispersity value in a range of from about 1.0 to about 1.5, and preferably in a range from about 1.0 to about 1.2.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Heparosan Synthase (HS) coding sequence yet is isolated away from, or purified free from, unrelated genomic DNA, for example, total *Pasteurella multocida*. Included within the term "DNA segment", are DNA segments and smaller fragments of such segments, and also recombinant vectors, including, for example, plasmids, cosmids, phage, viruses, and the like.

In one embodiment of the presently disclosed and claimed inventive concept(s), the biomaterial compositions of the presently disclosed and claimed inventive concept(s) may be produced using recombinant glycosaminoglycan transferases as described in the inventor's prior patent applications that have previously been incorporated herein. The recombinant glycosaminglycan transferases utilized in accordance with the presently disclosed and claimed inventive concept(s) may be selected from the group consisting of: a recombinant heparosan synthase having an amino acid sequence as set forth in at least one of SEQ ID NOS: 2, 4, and 6-8; a recombinant heparosan synthase encoded by the nucleotide sequence of at least one of SEQ ID NOS: 1, 3 and 5; a recombinant heparosan synthase encoded by a nucleotide sequence capable of hybridizing to a complement of the nucleotide sequence of at least one of SEQ ID NOS: 1, 3 and 5 under hybridization conditions comprising hybridization at a temperature of 68° C. in 5×SSC/5×Denhardt's solution/1.0% SDS, followed with washing in 3×SSC at 42° C.; a recombinant heparosan synthase encoded by a nucleotide sequence capable of hybridizing to a complement of a nucleotide sequence encoding an amino acid sequence as set forth in at least one of SEQ ID NOS:2, 4 and 6-8 under hybridization conditions comprising hybridization at a temperature of 68° C. in 5×SSC/5×Denhardt's solution/1.0% SDS, followed with washing in 3×SSC at 42° C.; a recombinant heparosan synthase encoded by a nucleotide sequence capable of hybridizing to a complement of the nucleotide sequence of at least one of SEQ ID NOS: 1, 3 and 5 under hybridization conditions comprising hybridization at a temperature of 30° C. in 5×SSC, 5×Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes; and a recombinant heparosan synthase encoded by a nucleotide sequence capable of hybridizing to a complement of a nucleotide sequence encoding an amino acid sequence as set forth in of at least one of SEQ ID NOS: 2, 4 and 6-8 under hybridization conditions comprising hybridization at a temperature of 30° C. in 5×SSC, 5×Denhardts reagent, 30% formamide for about 20 hours followed by washing twice in 2×SSC, 0.1% SDS at about 30° C. for about 15 min followed by 0.5×SSC, 0.1% SDS at about 30° C. for about 30 minutes. Recombinant heparosan synthases that fall within the scope of the description above and may be utilized in accordance with the presently disclosed and claimed inventive concept(s) have been described in detail in the inventor's issued U.S. Pat. No. 7,307,159, issued Dec. 11, 2007; and the inventor's patent applications U.S. Ser. No. 11/906,704, filed Oct. 3, 2007; and U.S. Ser. No. 10/814,752, filed Mar. 31, 2004; the entire contents of each of which are hereby expressly incorporated herein by reference.

The use of truncated glycosaminoglycan transferase genes to produce the biomaterial compositions of the presently disclosed and claimed inventive concept(s) also fall within the definition of preferred sequences as set forth above. For instance, the removal of the last 50 residues or the first 77 residues of PmHS1 (SEQ ID NOS: 7 and 8, respectively) does not inactivate its catalytic function (Kane et al., 2006). Those of ordinary skill in the art would appreciate that simple amino acid removal from either end of the GAG synthase sequence can be accomplished. The truncated versions of the sequence simply have to be checked for activity in order to determine if such a truncated sequence is still capable of producing GAGs. The other GAG synthases disclosed and claimed herein are also amenable to truncation or alteration with preservation of activity, and the uses of such truncated or alternated GAG synthases also fall within the scope of the presently disclosed and claimed inventive concept(s).

The recombinant glycosaminoglycan transferases utilized in accordance with the presently disclosed and claimed inventive concept(s) also encompass sequences essentially as set forth in SEQ ID NOS:1-8. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a heparosan polymer in vitro or in vivo. In the above examples X refers to either SEQ ID NO:1-8 or any additional sequences set forth herein, such as the truncated or mutated versions of pmHS1 that are contained generally in SEQ ID NOS:7-8.

The art is replete with examples of practitioner's ability to make structural changes to a nucleic acid segment (i.e., encoding conserved or semi-conserved amino acid substitutions) and still preserve its enzymatic or functional activity when expressed. See for special example of literature attesting to such: (1) Risler et al. Amino Acid Substitutions in Structurally Related Proteins. A Pattern Recognition Approach. J. Mol. Biol. 204:1019-1029 (1988) [. . . according to the observed exchangeability of amino acid side chains, only four groups could be delineated; (i) Ile and Val; (ii) Leu and Met, (iii) Lys, Arg, and Gln, and (iv) Tyr and Phe.]; (2) Niefind et al. Amino Acid Similarity Coefficients for Protein Modeling and Sequence Alignment Derived from Main-Chain Folding Anoles. J. Mol. Biol. 219:481-497 (1991) [similarity parameters allow amino acid substitutions to be designed]; and (3) Overington et al. Environment-Specific Amino Acid Substitution Tables Tertiary Templates and Prediction of Protein Folds, Protein Science 1:216-226 (1992) [Analysis of the pattern of observed substitutions as a function of local environment shows that there are distinct patterns . . . . Compatible changes can be made.]

It is widely recognized that a pair of distinct enzymes with even 30, 50 or 70% identity or similarity at the active site (of functional regions) thereof can possess the same catalytic activity. As most of the protein sequence is a scaffold for the active site, it is not required that all regions of the enzymes be exactly the same between functional enzyme homologs or analogs. In addition, some extra (non-catalytic) sequences may also be present, thus lowering the total protein similarity levels. Thus, functional regions (and not entire sequences) should be the basis for similarity comparisons between two enzymes.

These references and countless others, indicate that one of ordinary skill in the art, given a nucleic acid sequence or an amino acid, could make substitutions and changes to the nucleic acid sequence without changing its functionality (specific examples of such changes are given hereinafter and are generally set forth in SEQ ID NOS:7-8). Also, a substituted nucleic acid segment may be highly identical and retain its enzymatic activity with regard to its unadulterated parent, and yet still fail to hybridize thereto. Additionally, the present application discloses 4 enzymes and numerous mutants of these enzymes that still retain at least 50% of the enzymatic activity of the unmutated parent enzyme—i.e., ½ of the dual action transferase activity of the unadulterated parent. As such, variations of the sequences and enzymes that fall within the above-defined functional limitations have been disclosed in the applications incorporated by reference. One of ordinary skill in the art, given the present specification and the disclosures of the incorporated-by-reference parent applications, would be able to identify, isolate, create, and test DNA sequences and/or enzymes that produce natural or chimeric or hybrid GAG molecules. As such, the presently claimed and disclosed inventive concept(s) should not be regarded as being solely limited to the use of the specific sequences disclosed and/or incorporated by reference herein.

The presently disclosed and claimed inventive concept(s) may utilize nucleic acid segments encoding an enzymatically active HS from *P. multocida*-pmHS1 and/or PmHS2. One of ordinary skill in the art would appreciate that substitutions can be made to the pmHS1 or PmHS2 nucleic acid segments listed in SEQ ID NO:1, 3 and 5, respectively, without deviating outside the scope and claims of the presently disclosed and claimed inventive concept(s). Indeed, such changes have been made and are described hereinafter with respect to the mutants produced. Standardized and accepted functionally equivalent amino acid substitutions are presented in Table II. In addition, other analogous or homologous enzymes that are functionally equivalent to the disclosed synthase sequences would also be appreciated by those skilled in the art to be similarly useful in the methods of the presently disclosed and claimed inventive concept(s), that is, a new method to control precisely the size distribution of polysaccharides, namely glycosaminoglycans.

TABLE II

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Allowing for the degeneracy of the genetic code as well as conserved and semi-conserved substitutions, sequences which have between about 40% and about 99%; or more preferably, between about 60% and about 99%; or more preferably, between about 70% and about 99%; or more preferably, between about 80% and about 99%; or even more preferably, between about 90% and about 99% identity to the nucleotides of at least one of SEQ ID NO: 1, 3 and 5 will be sequences which are "essentially as set forth in at least one of SEQ ID NO: 1, 3 and 5." Sequences which are essentially the same as those set forth in at least one of SEQ ID NO: 1, 3 and 5 may also be functionally defined as sequences which are capable of hybridizing to a nucleic acid segment containing the complement of at least one of SEQ ID NO: 1, 3 and 5 under standard stringent hybridization conditions, "moderately stringent hybridization conditions," "less stringent hybridization conditions," or "low stringency hybridization conditions." Suitable standard or less stringent hybridization conditions will be well known to those of skill in the art and are clearly set forth hereinbelow. In a preferred embodiment, standard stringent hybridization conditions or less stringent hybridization conditions are utilized.

The terms "standard stringent hybridization conditions," "moderately stringent conditions," and less stringent hybridization conditions or "low stringency hybridization conditions" are used herein, describe those conditions under which substantially complementary nucleic acid segments will form standard Watson-Crick base-pairing and thus "hybridize" to one another. A number of factors are known that determine the specificity of binding or hybridization, such as pH; temperature; salt concentration; the presence of agents, such as formamide and dimethyl sulfoxide; the length of the segments that are hybridizing; and the like. There are various protocols for standard hybridization experiments. Depending on the relative similarity of the target DNA and the probe or query DNA, then the hybridization is performed under stringent, moderate, or under low or less stringent conditions.

The hybridizing portion of the hybridizing nucleic acids is typically at least about 14 nucleotides in length, and preferably between about 14 and about 100 nucleotides in length. The hybridizing portion of the hybridizing nucleic acid is at least about 60%, e.g., at least about 80% or at least about 90%, identical to a portion or all of a nucleic acid sequence encoding a heparin/heparosan synthase or its complement, such as SEQ ID NO:1, 3 or 5 or the complement thereof. Hybridization of the oligonucleotide probe to a nucleic acid sample typically is performed under standard or stringent hybridization conditions. Nucleic acid duplex or hybrid stability is expressed as the melting temperature or $T_m$, which is the temperature at which a probe nucleic acid sequence dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC, SSPE, or HPB). Then, assuming that 1% mismatching results in a 1° C. decrease in the $T_m$, the temperature of the final wash in the hybridization reaction is reduced accordingly (for example, if sequences having >95% identity with the probe are sought, the final wash temperature is decreased by about 5° C.). In practice, the change in $T_n$, can be between about 0.5° C. and about 1.5° C. per 1% mismatch. Examples of standard stringent hybridization conditions include hybridizing at about 68° C. in 5×SSC/5×Denhardt's solution/1.0% SDS, followed with washing in 0.2×SSC/0.1% SDS at room temperature or hybridizing in 1.8×HPB at about 30° C. to about 45° C. followed by washing a 0.2-0.5×HPB at about 45° C. Moderately stringent conditions include hybridizing as described above in 5×SSC\5×Denhardt's solution 1% SDS washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, (Cold Spring Harbor Press, N.Y.); and Ausubel et al. (eds.), 1995, Current Protocols in Molecular Biology, (John Wiley & Sons, N.Y.). Several examples of low stringency protocols include: (A) hybridizing in 5×SSC, 5×Denhardts reagent, 30% formamide at about 30° C. for about 20 hours followed by washing twice in 2×SSC, 0.1% SDS at about 30° C. for about 15 min followed by 0.5×SSC, 0.1% SDS at about 30° C. for about 30 min (FEMS Microbiology Letters, 2000, vol. 193, p. 99-103); (B) hybridizing in 5×SSC at about 45° C. overnight followed by washing with 2×SSC, then by 0.7× SSC at about 55° C. (J. Viological Methods, 1990, vol. 30, p. 141-150); or (C) hybridizing in 1.8×HPB at about 30° C. to about 45° C.; followed by washing in 1×HPB at 23° C.

The DNA segments that may be utilized to produce the biomaterial compositions of the presently disclosed and claimed inventive concept(s) encompass DNA segments encoding biologically functional equivalent HS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HS protein or to test HS mutants in order to examine HS activity at the molecular level or to produce HS mutants having changed or novel enzymatic activity and/or sugar substrate specificity.

Heparosan, a sugar polymer that is the natural biosynthetic precursor of heparin and heparan sulfate, has numerous characteristics that indicate that this material exhibits enhanced performance in a variety of medical applications or medical devices. In comparison to HA and heparin, two very structurally similar polymers used in many current applications in several large markets, heparosan is more stable in the body, as no naturally occurring enzymes degrade heparosan, and therefore the biomaterial compositions of the presently disclosed and claimed inventive concept(s) should have longer lifetimes compared to presently used biomaterials. In addition, heparosan interacts with fewer proteins (thus less fouling) and cells (thus less infiltration, scarring, or clotting) when compared to existing biomaterials.

In comparison to synthetic plastics or carbon, the natural hydrophilicity (aka water-loving) characteristics of heparosan also enhance tissue compatibility. Animal-derived proteins (e.g., collagen, bovine serum albumin) and calcium hydroxyapatite often have side effects, including but not limited to, eliciting an allergic response and/or stimulating granulation (5). On the other hand, even certain pathogenic bacteria use heparosan to hide in the body since this polymer is non-immunogenic (8-10). The biomaterial compositions of the presently disclosed and claimed inventive concept(s) produced from a non-animal source also promise to be free of adventitious agents (e.g., vertebrate viruses, prions) that could potentially contaminate animal- or human-derived sources.

Certain carbohydrates play roles in forming and maintaining the structures of multicellular organisms in addition to more familiar roles as nutrients for energy. Glycosaminoglycans [GAGs], long linear polysaccharides consisting of disaccharide repeats that contain an amino sugar, are well known to be essential in vertebrates (9, 11-15). The GAG structures possess many negative groups and are replete with hydroxyl groups; therefore, these sugars have a high capacity to adsorb water and ions. Heparin/heparan (backbone [β4GlcUA-α4GlcNAc]$_n$), chondroitin (backbone [β4GlcUA-β3GalNAc]$_n$), and hyaluronan (HA; backbone [β4GlcUA-β3GlcNAc]$_n$) are the three most prevalent GAGs in humans. Depending on the tissue and cell type, the GAGs are structural, adhesion, and/or signaling elements. A few clever microbes also produce extracellular polysaccharide coatings, called capsules, composed of GAG chains that serve as virulence factors (9, 10). The capsule is thought to assist in the evasion of host defenses such as phagocytosis and complement. As the microbial polysaccharide is identical or very similar to the host GAG, the antibody response is either very limited or non-existent.

Commercially, the GAG polymers are extracted from either animal tissues or bacterial cultures. The current market for GAGs is ~$4-8 billion and growing as more medical applications emerge. For example, heparin is the most used drug (an anticoagulant) in hospitals.

The production of the final heparinoid species found in animals requires multiple processing steps in vivo (12). The overall biosynthetic pathway for heparin/heparin sulfate in humans and other vertebrates is:

| Step | Repeat Unit | Common name of polymer |
|---|---|---|
| 1. polymerization of backbone | (GlcNAc-GlcUA)$_n$ | heparosan |
| 2. N-deacetylation and N-sulfation | (GlcNSO$_4$-GlcUA)$_n$ | N-sulfo-heparosan |
| 3. epimerization of acid unit* | (GlcNSO$_4$-IdoUA)$_n$ | — |
| 4. further O-sulfation of sugar-units* sulfate, | (GlcNSO$_4$[OSO$_4$]-IdoUA-[OSO$_4$])$_n$ | heparan heparin |

*note - epimerization and sulfation levels vary in tissues and developmental state, and between species.

In humans, heparosan only exists transiently, serving as a precursor to the more highly modified final products of heparan sulfate and heparin. In contrast, the bacterial strains set forth herein produce heparosan as their final product (16). Due to the less complex makeup of bacterial cells and to the relative ease with which their growth and expression can be modulated, harvesting a polymer from microbes is much easier, more scalable, and less expensive than extracting from animal tissues.

Dermal fillers serve as soft tissue replacements or augmentation agents (5, 6). The need for a dermal filler may arise from aging (loss of HA and elastin), trauma (loss of tissue), acne (severe pitting), and/or atrophy (certain wasting diseases including lipoatrophy). Three important characteristics that dermal fillers must possess include a) space-filling ability, b) maintenance of hydration, and c) biocompatibility (5). Currently, polysaccharides, proteins, plastics, and ceramics have been used as biomaterials in dermal fillers. With respect to aesthetic appearance and ease of implantation, softer injectable gels have better attributes; thus, polysaccharides and proteins are widely used. In addition to therapeutic uses, cosmetic applications are becoming more widespread. Alternatives to dermal filler treatment are the use of (i) plastic surgery (tightening the skin), (ii) nerve killing agents such as BOTOX® (relax muscles), and (iii) the use of autologous fat. Compared to dermal fillers, these alternatives are more invasive and/or leave the patient with an unnatural appearance (5, 6). For victims of trauma, scarring, or severe disease, an aim of the therapy is to instill more self-confidence and better disposition; this effect should not be discounted, as a patient's state of mind is important for overall healing.

A major goal of bioengineering is the design of implanted artificial devices to repair or to monitor the human body. High-strength polymers, durable alloys, and versatile semiconductors have many properties that make these materials desirable for bioengineering tasks. However, the human body has a wide range of defenses and responses that evolved to prevent infections and to remove foreign matter that hinders the utilization of modern man-made substances (17, 18). Improving the biocompatibility of these materials will remove a significant bottleneck in the advancement of bioengineering.

A leading example of a medical need for improved surface coatings lies in cardiovascular disease. Damage from this disease is a very prevalent and expensive problem; the patient's system is oxygen- and nutrient-starved due to poor blood flow. The availability of blood vessel grafts from transplants (either autologous or donor) is limited as well as expensive. Therefore, the ability to craft new artificial vessels is a goal, but will take more time to perfect due to the complex engineering and biological requirements. Another current, more approachable therapeutic intervention employs stents, artificial devices that prop open the inner cavity of a patient's blood vessel. As summated by Jordan & Chaikof, "The development of a clinically durable small-diameter vascular graft as well as permanently implantable biosensors and artificial organ systems that interface with blood, including the artificial heart, kidney, liver, and lung, remain limited by surface-induced thrombotic responses" (7). Thus, to advance this technology further, thromboresistant surface coatings are needed that inhibit: (i) protein and cell adsorption, (ii) thrombin and fibrin formation, and (iii) platelet activation and aggregation.

Artificial plastics (poly[lactide] in SCULPTRA® (Sanofi-Aventis) or poly[methylmethacrylate] in ARTECOLL® (Artes medical, Inc., San Diego, Calif.), ceramics (calcium hydroxyapatite in RADIESSE® (Bioform Medical, Inc., San Mateo, Calif.)) or pure carbon have utility for many therapeutic applications (1, 5, 7, 18), but in many respects, their chemical and physical properties are not as optimal as polysaccharides for the targeted goals of dermal fillers or surface coatings. The most critical issues are lack of good wettability (due to poor interaction with water) and/or hardness (leading to an unnatural feel or brittleness). The presently claimed and disclosed inventive concept(s) is related to the use of heparosan to replace and supplant useful sugar polymers that are hydrophilic (water loving) and may be prepared in a soft form.

In addition to HA and heparin, other polysaccharides such as dextran ($[\alpha6Glc]_n$), cellulose ($[\beta4Glc]_n$), or chitosan ($[\beta4GlcN]_n$) have many useful properties, but since they are not naturally anionic (negatively charged), these polymers do not mimic the natural extracellular matrix or blood vessel surfaces. Cellulose and dextran can be chemically transformed into charged polymers that help increase their biocompatibility and improve their general physicochemical properties, but harsh conditions are required leading to batch-to-batch variability and quality issues. On the other hand, GAGs, the natural polymers, have intrinsic negative charges.

HA and heparin have been employed as biomaterial coatings for vascular prosthesis and stents (artificial blood vessels and supports), as well as coatings on intraocular lenses and soft-tissue prostheses (7, 22). The rationale is to prevent blood clotting, enhance fouling resistance, and prevent post-surgery adhesion (when organs stick together in an undesirable fashion). The biomaterial compositions of the presently disclosed and claimed inventive concept(s) should also be suitable as a coating, as described in greater detail herein after.

A key advantage with heparosan is that it has increased biostability in the extracellular matrix when compared to other GAGs. As with most compounds synthesized in the body, new molecules are made, and after serving their purpose, are broken down into smaller constituents for recycling. Heparin and heparan sulfate are eventually degraded and turned over by a single enzyme known as heparanase (23, 24). Experimental challenge of heparosan and N-sulfo-heparosan with heparanase, however, shows that these polymers lacking O-sulfation are not sensitive to enzyme action in vitro (25, 26). These findings demonstrate that heparosan is not fragmented enzymatically in the body. Overall, this indicates that heparosan is a very stable biomaterial.

Another glycosaminoglycan, hyaluronan [HA], is very abundant in the human body and is currently employed as a biomaterial for many applications (2, 5, 6, 27, 28). However, a family of degradative enzymes, called hyaluronidases, attacks HA in the body during normal turnover (29) in a fashion similar to the activity of heparanase. Heparosan, although it possesses the same sugar unit composition, has different intersugar linkages that are not cleavable by hyaluronidases (30) (FIG. 1). Thus heparosan is expected to be more long-lived than HA, a currently useful biomaterial, in the human body. For dermal fillers, this feature translates into a reduction in the number of injections that need to be performed (currently ~2-3 per year). For the HA-based products with the largest market share, the polysaccharide chains are cross-linked, which hinders hyaluronidase digestion (6), but cleavage still occurs; such cleavage weakens and finally destroys the gel network. The devices of the presently claimed and disclosed inventive concept(s), which have longer lasting coatings, should not need to be removed/replaced as quickly and/or should have lower failure/complication rates when compared to existing biomaterial devices.

Heparosan polymer is predicted to be much more stable in the extracellular compartment than HA as described above. However, if heparosan fragments are generated (by reactive oxygen species) and then internalized into the lysosome, these chains will be degraded by resident beta-glucosidase and beta-hexosaminidase enzymes (which remove one sugar at a time from chain termini) like heparin or HA (31). Therefore, the heparosan polymer is biodegradable and not permanent and thus should not cause a lysosomal storage problem. A key advantage with heparosan is that it has increased biostability in the extracellular matrix when compared to other GAGs.

Heparosan is a transiently existing sugar polymer in mammals. Generally speaking, molecules that normally exist in the body are regarded as "self" and therefore not subjected to attack by antibodies, phagocytes, or complement system. This fact is employed by certain pathogenic bacteria that coat themselves with molecules identical or very similar to host molecules. Two different types of bacteria, *Pasteurella multocida* Type D (16) and *Escherichia coli* K5 (32), both produce heparosan coatings that are important for camouflage and hiding from host defenses (8, 32). Therefore, heparosan is predicted to be relatively invisible to the frontline human defenses.

The normal roles of heparin/heparan sulfate in vertebrates include, but are not limited to, binding coagulation factors (inhibiting blood clotting) and growth factors (signaling cells to proliferate or differentiate) (33). The key structures of heparin/heparan sulfate that are recognized by these factors include a variety of O-sulfation patterns and the presence of iduronic acid [IdoUA]; in general, polymers without these modifications do not stimulate clotting or cell growth (33). Therefore, heparosan-based gels or coatings should not provoke unwanted clotting or cellular growth/modulation.

Heparan sulfate also interacts with extracellular matrix molecules including collagen (33), but heparosan should not interact strongly under normal physiological conditions. Collagen deposition is part of the normal wound repair process; thus, heparosan gels and coatings should avoid triggering scarring. Other proteins that do bind heparin/heparan sulfate and several cell types with other protein receptors for heparan sulfate/heparin should not adhere to heparosan. Certain chemotactic factors that bind heparin are not known to bind heparosan (33). Therefore, cells should not seek out and infiltrate heparosan-based materials, thereby compromising their integrity or changing their properties.

Hyaluronan [HA] is normally made as a large molecular weight polysaccharide ($n=10^{3-4}$ sugar units), but over time (~day to weeks) HA is degraded into smaller oligosaccharides (n=4-20 units) (29, 34). These latter fragments have two biological activities (35-37) that may have direct impacts on the body implanted with a HA-based biomaterial. First, these fragments are angiogenic, and thereby cause new blood vessels to sprout. Second, the fragments appear to constitute a "danger signal" where the body is alerted to potential pathogen attack or damage. In both cases, these normal repair systems will re-model or alter the tissues near the implanted HA-derived biomaterial or HA-coated surface, which may be detrimental. Both the angiogenesis and the "danger signal" events are initiated by HA oligosaccharides binding to cell surface receptors; CD44 and Toll-like receptors, respectively, appear to be the signaling proteins (38, 39). Heparosan, which is structurally similar to HA, does not bind to CD44 (preliminary results, DeAngelis laboratory). Certain lymphocytes (white blood cells) with surface CD44 that interact with HA also should not recognize heparosan; it is thought that CD44 helps the cell move from the blood into tissues (extravasion). Heparosan should not serve as such a docking site, thereby limiting lymphocyte infiltration of the implanted biomaterial or surrounding area.

Overall, heparosan is more biologically inert than HA or heparin, both popular and highly profitable biomaterials. For dermal fillers and reconstructive surgery applications, the space-filling, moisture-retaining characteristics of the biomaterial are desired without triggering subsequent events such as angiogenesis, inflammation or infiltration cascades. Similarly, heparosan-coated surfaces should freely interact with water, but proteins and cells should not bind strongly to the polymer.

Some medical applications may require a bioactive material or functionalized surface rather than the inert properties of heparosan. Heparosan can still potentially serve as the scaffold containing or releasing these bioactive molecules.

Currently, several approved biomaterials (including collagen and some HA) have limitations due to animal-derived or human-derived components (5, 6). For example, Baxter had to recall batches of porcine heparin in early 2008. Adventitious agents such as viruses or prions may not be completely removed during processing. Bovine collagen is potentially the largest concern in light of 'mad cow disease', but human adventitious agents may also be transferred from the tissue bank material or cell lines. In addition, hitherto unrecognized or emerging pathogens, as well as very low pathogen levels (i.e., due to "false-negative" or erroneous tests), are always a possibility with vertebrate-derived materials. Therefore, the FDA provided a guidance statement in 2004 that only synthetic or plant-based materials should be used in future therapeutics, if possible. Fortunately, the bacterially derived heparosan biomaterial compositions of the presently disclosed and claimed inventive concept(s) cannot possess prions, HIV or hepatitis virus, etc., since these contaminants are only associated with vertebrates.

In addition to containing potential adventitious agents, animal proteins are usually recognized by the human immune system because their amino acid sequences are not identical to man. Some human individuals are sensitive and thus cannot use the cow-derived collagen or the chicken comb-derived HA (5). Currently, skin tests are used to screen for hypersensitivity or allergenicity. However, certain individuals may also become sensitive or reactive to materials after implantation; in effect, such a person will have been vaccinated with a foreign material. This effect may be more problematic if the same material is given in several applications, and a slight response escalates after the immune system is boosted multiple times. With dermal filler procedures, multiple applications are often standard. If a detrimental side effect occurs once a gel is implanted, it is virtually impossible to remove all offending material.

Even if human collagen is employed, after extraction and processing, its denatured or unfolded state may potentially stimulate some connective tissue diseases such as rheumatoid arthritis, systemic lupus erythematosus, polymyositis, or dermatomyositis (5). On the other hand, heparosan should not create an autoimmune response against connective tissue proteins.

Human-derived material is used for two products, CYMETRA™ (acellular dermal tissue derivative; LifeCell Corp., Branchburg, N.J.) and collagen allograft (fibroblast culture extracts). In addition to possible safety concerns, these materials are limited (derived from tissue bank material) and/or expensive (human cell cultured in vitro). On the other hand, heparosan polysaccharide from bacterial fermentation can be an abundant, renewable resource.

The chemical and physical structures shared by HA, heparin and heparosan result in their ability to bind large amounts of water and ions to expand tissues and interact well with aqueous fluids of the body. These are major beneficial attributes for a dermal filler or a coating.

In summary, the key features of the biomaterial compositions of the presently disclosed and claimed inventive concept(s) that provide improved performance for use in dermal fillers for reconstructive surgery and in non-fouling, non-clogging medical devices, compared to existing HA or heparin products, include, but are not limited to: (a) resistance to enzyme-mediated attack; (b) lack of clotting factor, chemoattractant, and growth factor binding sites; (c) lack of known cell signaling or attachment domains; (d) lack of vertebrate-derived proteins and adventitious agents; and (e) lack of protein-based allergens or immunogens.

Examples are provided hereinbelow. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

EXAMPLES

Production of Heparosan Polysaccharide.

Certain *Pasteurella multocida* bacteria make an extracellular coating composed of unsulfated heparosan polymer that is readily harvested from the culture media. There is only one other known source of unsulfated, underivatized heparosan: *Escherichia coli* K5. A major benefit of the *Pasteurella* heparosan over *E. coli* K5 heparosan and mammal heparin is that it has a higher molecular weight, ~200-300 kDa (16); therefore, gels formed of the *Pasteurella* heparosan should be easier to produce.

Figure 2:
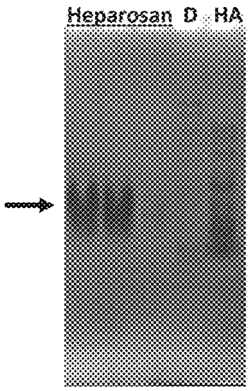
FIG. 2 depicts a gel analysis demonstrating production of heparosan polysaccharide. A 0.6% gel with Stain-all detection shows the *Pasteurella multocida* heparosan (marked with arrow) in comparison to DNA ladder (D=Bioline Hyper ladder) and a HA ladder (HA=Hylaose Hi and lo Ladders combined).

Small-scale shake flasks of the *Pasteurella* microbe were grown in synthetic media for 20-36 hours. Centrifugation was used to remove the cells. The spent media was solvent extracted, then anion exchange-purified. The resulting heparosan is substantially free of protein (as judged by Bradford assays and SDS-PAGE gels with Coomassie staining) and DNA (as judged by agarose gels with ethidium bromide staining; see FIG. 2) contamination. This material (~0.2-0.5 grams/liter yield) formed a fluffy, salt-free, white powder suitable for chemical cross-linking or coating reactions.

Production of Polysaccharide Gels.

Figure 3:
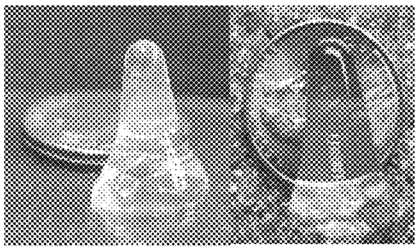
FIG. 3 depicts production of heparosan polysaccharide gels. *P. multocida* heparosan was cross-linked with DVS in a conical tube, washed, and the gel was removed. The transparent gel retains its shape even when not supported by liquid. Tighter or looser gels and viscous liquids are made by altering the reaction stoichiometry and conditions.

Cross-linking agents, such as but not limited to, divinyl sulfone (DVS) or di-epoxides, were used to make a variety of GAG gels including a small amount of a prototype heparosan gel (FIG. 3). The gel is stable in vitro, maintains its physical shape, but is soft as desired.

Production of Polysaccharide Coatings.

Figure 4:
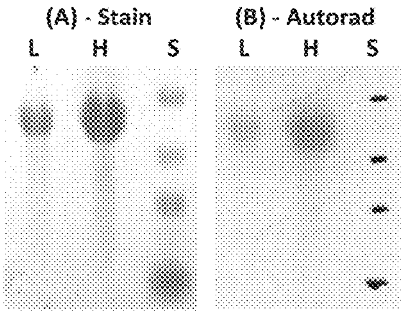
FIG. 4 depicts agarose gel analysis demonstrating production of polysaccharide coatings utilizing a $^{125}$I-HA probe. A radioactive Bolton-Hunter labeled HA tetramer primer was extended by a synchronized polymerization reaction with PmHAS to make a monodisperse HA probe. Stains-all dye (A) and the X-ray film (B) both show a single major ~250 kDa product (L, low and H, high sample loadings; S, HA size standards=310, 214, 110, 27 kDa from top to bottom, Hyalose LoLadder). The probe's gamma ray emissions are readily followed without destructive testing of the coated surfaces facilitating quantitation.

Radioactive $^{125}$I-labeled HA (FIG. 4), a polymer with the same chemical reactivity and molecular weight (~300 kDa) as the heparosan produced above, was incubated with epoxy-activated steel or silicone (obtained from AeonClad Coatings, LLC) and then washed extensively. The radioactivity of the materials was checked in a gamma counter.

As shown in Table III, the radioactive sugar was coupled to both surfaces; in contrast, parallel control surfaces without the epoxy coating did not bind the sugar substantially. The coatings were relatively stable for at least 4 weeks (the length of the initial study) after incubation in saline (multiple washes over time).

Stability of Biomaterial Compositions in Human Plasma.

Figure 5:
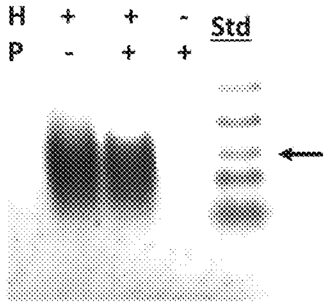
FIG. 5 illustrates challenge of heparosan with human plasma. This agarose gel (0.9%, 1×TAE) with Stains-all detection shows that the molecular weight of the original heparosan (H) is unchanged even after incubation with plasma (P) after overnight incubation at 37° C. (Std, HA lo-ladder, the 214 kDa band is marked with an arrow; Hyalose, LLC, Oklahoma City). Heparosan is a stable biomaterial.

FIG. 5 illustrates that the biomaterial compositions of the presently disclosed and claimed inventive concept(s) are not degraded in human blood. Fresh blood was obtained from a finger stick of a healthy human male, diluted 1:1 with PBS (Phosphate-buffered saline, pH 7.4), and the cells were removed by gentle centrifugation (300×g, 2 min). The plasma in the supernatant was mixed with a heparosan solution in PBS (0.7 mg/ml polymer) in a 1:2 vol/vol ratio and then incubated overnight at 37° C. A 10 microliter sample was subjected to gel electrophoresis. As controls, plasma alone or heparosan alone were tested in parallel. As evidenced by FIG. 5, the molecular weight of the original heparosan (H) is unchanged even after incubation with plasma (P) after overnight incubation. Therefore, the heparosan biomaterial compositions of the presently disclosed and claimed inventive concept(s) are stable biomaterials.

TABLE III

Addition of HA (a heparosan polymer proxy) to Steel or Silicone and Stability Testing

| | Coating Buffer | | | |
|---|---|---|---|---|
| | 0.1M Na phospate | 1.0M Na borate | $^{125}$I-HA (dpm) | |
| Material | pH 8 | pH 9 | time 0 | 4 weeks |
| Steel | | | | |
| Epoxy-activated | | + | 970 | 540 |
| No activation | | + | 95 | 32 |
| Epoxy-activated | + | | 1030 | 540 |

TABLE III-continued

Addition of HA (a heparosan polymer proxy) to Steel or Silicone and Stability Testing

| | Coating Buffer | | | |
|---|---|---|---|---|
| | 0.1M Na phospate | 1.0M Na borate | $^{125}$I-HA (dpm) | |
| Material | pH 8 | pH 9 | time 0 | 4 weeks |
| No activation Silicone | + | | 100 | 46 |
| Epoxy-activated | + | | 1330 | 600 |
| No activation | + | | 220 | 85 |
| Epoxy-activated | | + | 900 | 430 |
| No activation | | + | 170 | 60 |

Discussion of Examples

Many *P. multocida* isolates produce GAG or GAG-like molecules (8). Carter Type D *P. multocida*, the major causative agent of fowl cholera and pasteurellosis, makes a heparosan capsule. A single polypeptide, the heparosan synthase, PmHS1, polymerizes the sugar chain by transferring both GlcUA and GlcNAc (30). In *E. coli* K5, at least two enzymes, KfiA, the alpha-GlcNAc transferase, and KfiC, the beta-GlcUA-transferase, (and perhaps KfiB, a protein of unknown function) work in concert to form the disaccharide repeat (40).

*P. multocida* Type D (or an improved recombinant version) should be a more economical and useful source of heparosan than *E. coli* K5 for several reasons. The former microbe has a higher intrinsic biosynthetic capacity for capsule production. The *Pasteurella* capsule radius often exceeds the cell diameter when observed by light microscopy of India Ink-prepared cells. On the other hand, visualization of the meager *E. coli* K5 capsule often requires electron microscopy. From a safety standpoint, *E. coli* K5 is a human pathogen, while Type D *Pasteurella* has only been reported to cause disease in animals. Furthermore, with respect to recombinant gene manipulation to create better production hosts, the benefits of handling only a single gene encoding either PmHS1 or PmHS2, dual action synthases, in comparison to utilizing KfiA, KfiB, & KfiC, are obvious.

In some aspects of the presently disclosed and claimed inventive concept(s), the heparosan of the biomaterial compositions of the presently disclosed and claimed inventive concept(s) will be processed prior to use in the body to mold its characteristics. Solutions of heparosan polymer are viscous, but will eventually diffuse and dilute from the original site of injection or placement; thus, a more immobilized form may be desired, such as but not limited to, a gel or a particulate suspension. In this form, the material may be covalently cross-linked by chemical means to provide a long-lasting form. In contrast, non-covalent ionic bridge complexes (e.g., with divalent metal cations, etc) will weaken and fall apart over a much shorter time scale; thus, such formulations are not as ideal as the cross-linked materials; however, such materials are still encompassed by the presently disclosed and claimed inventive concept(s).

Numerous gel-forming chemistries, from exotic to crude, are possible. Two independent types of cross-linkers have been investigated herein: a) divinyl sulfone and b) diepoxide. Several key factors considered in choosing these two cross-linkers included (a) the ability to form stable gels in one chemical step with a single reagent, and (b) the previous success of these reagents with HA resulted in two widely employed, FDA-approved gels (41).

Figure 6:
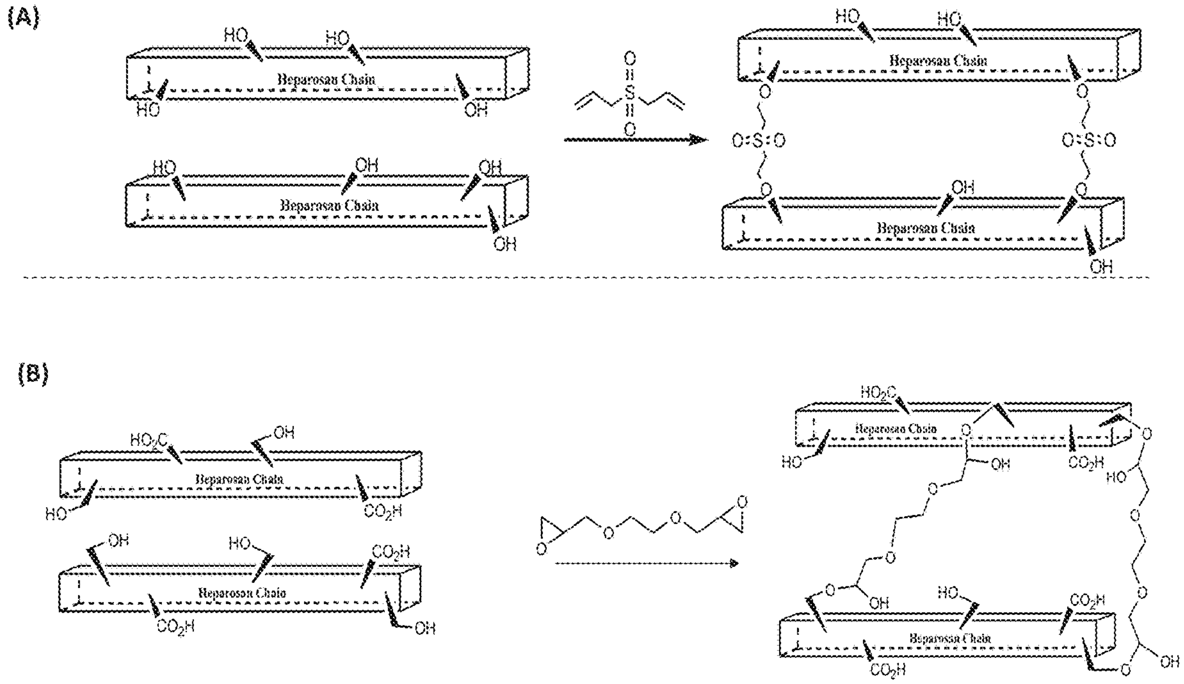
FIG. 6 illustrates reactions and structures of Heparosan-based gels. A: a Heparosan-based gel with a structure similar to HYLAFORM® made with divinyl sulfone. B: a Heparosan-based gel with a structure similar to RESTYLANE® made with 1,2-diethanediol diglycidyl ether.

The size distribution of HA used for existing gels on the market ranges in size from ~800-1,000 kDa for bacterial HA to ~2,000-4,000 kDa for chicken-derived HA. HYLAFORM® (Genzyme) is made with dimethyl sulfone while RESTYLANE® (QMed) employs the diepoxide, 1,2-diethanediol diglycidyl ether (FIG. 6). Both HA-based products have very desirable physical properties; thus, heparosan with a similar structure should also be useful. The heparosan polymer derived from *Pasteurella multocida* Type D has a molecular mass (~200-300 kDa) that should be sufficient for cross-linking at achievable concentrations. On the other hand, the smaller polymer from *E. coli* K5 is only ~30-80 kDa and thus more difficult to effectively cross-link at readily obtainable sugar concentrations.

The selected cross-linkers have the ability to react simultaneously with two hydroxyl groups of the sugar polymers, thus allowing multiple chains to be covalently connected. A vast network of cross-linked chains is created, thereby forming a sugar gel.

The presently claimed and disclosed inventive concept(s) demonstrates that heparosan is a better biomaterial for certain approachable medical applications. A comparison of the characteristics and properties of the presently disclosed and claimed inventive concept(s) to existing technologies is listed in Table IV.

The presently claimed and disclosed inventive concept(s) includes a method to apply a heparosan polysaccharide surface coating that will shield medical device components from the detrimental responses of the body to foreign matter. Interestingly, there is a natural prototype of such surface coating: certain pathogenic bacteria utilize an external shell of the same polysaccharide as camouflage to grow relatively unhindered in the body during infection (8). Therefore, the presently claimed and disclosed inventive concept(s) provides a biocompatible interface to bridge the gap between artificial substances and living flesh and blood.

Targets that may be coated by the presently disclosed and claimed inventive concept(s) include, but are not limited to, surgical steel, widely used for stents, and medical-grade silicone rubber, widely used for piping fluids and blood. The properties and characteristics of the presently disclosed and claimed inventive concept(s) and existing medical device surface coatings are outlined in Table V.

Plasma deposition is a proven process to deposit thin films directly from a gas state onto a solid substrate. Plasma deposition methods typically balance the benefits of extended coating times with the negatives of surface ablation that occurs with extended plasma exposure. Most plasma deposition methods use a continuous discharge to create the plasma state. However, extended exposure can begin to erode not only the newly formed coating but also the underlying material. AeonClad's advanced single-step, solvent-free, pulsed process eliminates surface ablation by rapidly creating a protective polymer layer upon which any number of films can be deposited (42,43). Therefore, the presently disclosed and claimed inventive concept(s) includes methods of providing a coating of the heparosan biomaterial on the surface of a substrate utilizing such plasma deposition methods.

TABLE IV

Comparison of Heparosan and Existing Surgical Biomaterials for Dermal Filler Applications.

| Key Variable | Project Target | Current Practice | Associated Barrier of Current Procedure | Presently disclosed and claimed inventive concept(s)'s Innovative Approaches |
|---|---|---|---|---|
| Coating Stability | Long lasting (weeks-months). | HA, heparin, Bovine serum albumin (BSA) | Degraded by body's natural enzymes | Use heparosan, a polymer that is not enzymatically digested in human body. |
| | | Carbon (C) | — | |
| | | Lipids (L) | Shed from surface | |
| Wettability | Freely interacts with water. | BSA, HA, heparin, L | — | Use water-loving heparosan polymer. |
| | | C | Hydrophobic | |
| Fouling, Clotting | Surface does not bind proteins or cells. | HA, heparin | Blood cells & clotting factors bind | Use relatively biologically inert heparosan polymer. |
| | | BSA, C, L | — | |
| Disease Transmission | Zero risk of animal virus or prions. | HA [chicken], CG | Potential risk | Use non-animal, bacterially derived heparosan. |
| | | HA [bacterial], PP, CHP | — | |

TABLE V

Comparison of Heparosan and Existing Biomaterials for Surface Coating Applications.

| Key Variable | Project Target | Current Practice | Associated Barrier of Current Procedure | Presently disclosed and claimed inventive concept(s)'s Innovative Approaches |
|---|---|---|---|---|
| Semi-stable Gel Formation | Injectable, Soft, long-lasting | Hyaluronan Gel (HA) Collagen Gel (CG) | Too short lifetime | Use heparosan, a polymer that is not |

TABLE V-continued

| Comparison of Heparosan and Existing Biomaterials for Surface Coating Applications. | | | | |
|---|---|---|---|---|
| Key Variable | Project Target | Current Practice | Associated Barrier of Current Procedure | Presently disclosed and claimed inventive concept(s)'s Innovative Approaches |
| | (>12-24 months), but not permanent gel. | Plastic Particles (PP)<br>Ca Hydroxyapatite Particles (CHP) | Grainy appearance & too long lifetime<br>Grainy appearance too long lifetime, & cannot inject easily | enzymatically digested in human body, and is not a coarse, hard material. |
| Immunogenicity, Allergenicity | No antibody generation. | HA [bacterial], PP, CHP<br>HA [chicken], CG [bovine>human] | —<br>Immune or allergic response | Use heparosan polymer that looks 'human' and does not trigger immune system. |
| Infiltration | Reduce cell adhesion and/or signaling. | HA<br>PP, CHP<br>CG | Proteins & cells bind<br>—<br>Cells bind | Use heparosan polymer that lacks known adhesion domains or chemotactic signals. |
| Disease Transmission | Zero risk of human or animal virus and/or prions. | HA [chicken], CG<br>HA [bacterial], PP, CHP | Potential risk<br>— | Use non-animal, bacterially derived heparosan. |
| X-ray Imaging Compatible | No opaque or marked areas. | HA, CG<br>PP, CHP | —<br>Obscures images | Use X-ray-transparent heparosan. |
| Abundant Resource | Renewable & not overly expensive to produce. | CG [human]<br>HA, CHP, PP, CHP | Limited tissue bank supply or cell culture derived (costly)<br>— | Use heparosan made via bacterial fermentation. |

Materials and Methods

Heparosan Production and Testing:

*P. multocida* Type D cells were grown in synthetic media at 37° C. in shake flasks for ~24 hrs. Spent culture medium (the liquid part of culture after microbial cells are removed) was harvested (by centrifugation at 10,000×g, 20 min) and deproteinized (solvent extraction with chloroform) (16). The very large anionic heparosan polymer (~200-300 kDa) was isolated via ultrafiltration (30 kDa molecular weight cut-off; Amicon) and ion exchange chromatography (NaCl gradient on Q-Sepharose; Pharmacia). Overall, the cells (with the vast majority of contaminants) and the small molecules (which would consume cross links or activated surface) were readily removed. Any endotoxin was removed by passage through an immobilized polymyxin column (Pierce); the material was then tested with a *Limulus* amoebacyte-based assay (Cambrex Corporation, East Rutherford, N.J.) to assure that the heparosan contains <0.05 endotoxin units/mg solid (based on USP guidelines for medical devices).

The yield and molecular weight size distribution of the heparosan in the spent media was checked by a) carbazole assays for uronic acid (44) and b) agarose gel electrophoresis (1×TAE buffer, 0.8-1.5% agarose) followed by Stains-All detection (45). The carbazole assay is a spectrophotometric chemical assay that measures the amount of uronic acid in the sample via production of a pink color; every other sugar in the heparosan chain is a glucuronic acid. The heparosan polymer size was determined by comparison to monodisperse HA size standards (HA Lo-Ladder, Hyalose, LLC) run on gels. The detection limit of the carbazole and the gel assays is ~5-15 micrograms of polymer. It is estimated that ~3-5 grams of heparosan polymer are required for gel and coating preparation.

Gel Synthesis Overview.

The porosity or strength of a polysaccharide-based gel may be modulated by altering (a) the polymer concentrations and/or (b) the ratio of polymer and cross-linker. Less polymer per unit volume (i.e., low concentration) will have a looser structure. At a given sugar polymer concentration, more cross-links result in stronger gels with small pores while less cross-links result in softer gels with large pores. Therefore, a parallel series of reactions with varying amounts of cross-linker and/or heparosan are made and analyzed. The initial starting range for reaction conditions is 10-100 mg/ml heparosan cross-linked with 50:1 to 5:1 w/w polymer/crosslinker ratios in 0.1-0.25M NaOH (pH ≥9); divinyl sulfone is reacted at 20° C. for 1 hour while 1,2-diethanediol diglycidyl ether is used at 40° C. for 2-4 hours. These selections are based on the preparation of HYLAFORM® and RESTYLANE® products (U.S. Pat. Nos. 4,582,865 and 5,827,937, respectively); however, the presently disclosed and claimed inventive concept(s) also includes an extension of this range as well. The use of very alkaline NaOH solutions also helps to sanitize the gels, an added bonus for processing.

After the cross-linking reaction, the gel was washed repeatedly with water and saline buffer to remove any excess reagents (NaOH, cross-linker) and then was subjected to chemophysical and biological analysis. In the most widely employed embodiment of dermal fillers, a slurry or suspension of gel particles (created by sieving through defined mesh and/or sonic disruption) was injected.

Coating Synthesis Overview.

Two steps were employed: first, plasma-activation of the surface and second, chemical reaction with heparosan. A variable duty cycle pulsed radio frequency (RF) plasma technique is used (42,43). Using an algorithm, the optimum duty cycle (the plasma on and off pulse widths can be independently varied from 0.01-100 millisec), coating time (e.g., 20 minutes to add 100 nm thickness coating), monomer mixture, and peak deposition rate for each coating and substrate are optimized. The film formation occurs predominately during the plasma off times via a free radical mechanism, as initiated by the reactive species produced during the very brief plasma on periods. Basically, the use of modulated frequency pulses allows much higher levels of retention of monomer reactive group functionalities, as well as widens the range of chemistries available, in the polymer films produced. Importantly, it is also possible to vary, in a highly controlled fashion, the surface density of the reactive groups so introduced. The pulsed RF plasma method provides the flexibility to produce many types of coatings including those with antimicrobial, anti-thrombogenic, lubricious, and biocompatible features.

The initial surfaces are (a) silicone tubing (Silastic medical grade, Dow Corning) and (b) surgical steel coated with the reagent glycidal methacrylate; under low duty cycle pulsed plasma conditions, this reagent forms epoxide-containing surfaces for simple subsequent heparosan coupling reactions (as in Table III). Preliminary optimization of the epoxide surface coating thickness (to form a water-stable layer with good surface reactivity) has already been performed by AeonClad, but several thicknesses for use with heparosan will also be explored. As mentioned earlier, HA, a close chemical proxy for heparosan, has been immobilized in a stable form to the initial samples of activated steel and silicone.

Other possible cross-linkers may also be used. For example, coatings that provide amino groups that will couple to the GAG's acid groups in the presence of carbodiimide, if needed. Furthermore, with both the epoxide or the amine surfaces, spacer molecules can be readily introduced which will permit attachment of the heparson at various distances from the solid substrates.

The expoxide-based coated surfaces have been reacted with hydroxyls of heparosan at high pH (in analogy to gel synthesis, FIG. 3 B). For this procedure, acidic conditions to couple to the surface-bound epoxides via the carboxylate groups are also possible. The activated surface is flooded with the heparosan solution in the appropriate buffer (0.1-0.25M NaOH or 0.1M Na phosphate, pH 2-5) for several hours at 22-40° C. The solution is then removed and the surface is washed thoroughly (water, saline, etc.) before testing. Unactivated surfaces (negative control) as well as surfaces have lower signals in comparison.

Although the foregoing has been described in detail by way of illustration and example for purposes of clarity of understanding, it will be obvious to those skilled in the art that certain changes and modifications may be practiced without departing from the spirit and scope thereof, as described in this specification and as defined in the appended claims below.

REFERENCES

The following references, to the extent that they provide exemplary procedural or other details supplementary to those set forth herein, are specifically incorporated herein by reference in their entirety as though set forth herein particular.

1. Burg, K. J., Porter, S., and Kellam, J. F. (2000) Biomaterial developments for bone tissue engineering *Biomaterials* 21, 2347-2359
2. Luo, Y., Kirker, K. R., and Prestwich, G. D. (2000) Cross-linked hyaluronic acid hydrogel films: new biomaterials for drug delivery *J Control Release* 69, 169-184
3. Morra, M. (2005) Engineering of biomaterials surfaces by hyaluronan *Biomacromolecules* 6, 1205-1223
4. Olivier, V., Faucheux, N., and Hardouin, P. (2004) Biomaterial challenges and approaches to stem cell use in bone reconstructive surgery *Drug Discov Today* 9, 803-811
5. Johl, S. S., and Burgett, R. A. (2006) Dermal filler agents: a practical review *Curr Opin Ophthalmol* 17, 471-479
6. Eppley, B. L., and Dadvand, B. (2006) Injectable soft-tissue fillers: clinical overview *Plast Reconstr Surg* 118, 98e-106e
7. Jordan, S. W., and Chaikof, E. L. (2007) Novel thromboresistant materials *J Vasc Surg* 45 Suppl A, A104-115
8. DeAngelis, P. L. (2002) Microbial glycosaminoglycan glycosyltransferases *Glycobiology* 12, 9R-16R
9. DeAngelis, P. L. (2002) Evolution of glycosaminoglycans and their glycosyltransferases: Implications for the extracellular matrices of animals and the capsules of pathogenic bacteria *Anatomical Record* 268, 317-326
10. Jann, K., and Jann, B. (1992) Capsules of *Escherichia coli*, expression and biological significance *Can J Microbiol* 38, 705-710
11. Sugahara, K., and Kitagawa, H. (2002) Heparin and heparan sulfate biosynthesis *IUBMB Life* 54, 163-175
12. Esko, J. D., and Lindahl, U. (2001) Molecular diversity of heparan sulfate *J Clin Invest* 108, 169-173
13. Hardingham, T. E., and Fosang, A. J. (1992) Proteoglycans: many forms and many functions *Faseb* 16, 861-870
14. Laurent, T. C., and Fraser, J. R. (1992) Hyaluronan *Faseb J* 6, 2397-2404
15. Toole, B. P. (2000) Hyaluronan is not just a goo! *J Clin Invest* 106, 335-336
16. DeAngelis, P. L., Gunay, N. S., Toida, T., Mao, W. J., and Linhardt, R. J. (2002) Identification of the capsular polysaccharides of Type D and F *Pasteurella multocida* as unmodified heparin and chondroitin, respectively *Carbohydr Res* 337, 1547-1552
17. Gorbet, M. B., and Sefton, M. V. (2004) Biomaterial-associated thrombosis: roles of coagulation factors, complement, platelets and leukocytes *Biomaterials* 25, 5681-5703
18. Ma, Z., Mao, Z., and Gao, C. (2007) Surface modification and property analysis of biomedical polymers used for tissue engineering *Colloids Surf B Biointerfaces*
19. Massia, S. P., Holecko, M. M., and Ehteshami, G. R. (2004) In vitro assessment of bioactive coatings for neural implant applications *J Biomed Mater Res A* 68, 177-186
20. Czaja, W. K., Young, D. J., Kawecki, M., and Brown, R. M., Jr. (2007) The future prospects of microbial cellulose in biomedical applications *Biomacromolecules* 8, 1-12
21. Chandy, T., and Sharma, C. P. (1990) Chitosan—as a biomaterial *Biomater Artif Cells Artif Organs* 18, 1-24
22. Allison, D. D., and Grande-Allen, K. J. (2006) Review. Hyaluronan: a powerful tissue engineering tool *Tissue Eng* 12, 2131-2140
23. McKenzie, E., Young, K., Hircock, M., Bennett, J., Bhaman, M., Felix, R., Turner, P., Stamps, A., McMillan, D., Saville, G., Ng, S., Mason, S., Snell, D., Schofield, D., Gong, H., Townsend, R., Gallagher, J., Page, M., Parekh, R., and Stubberfield, C. (2003) Biochemical characterization of the active heterodimer form of human heparanase (Hpa1) protein expressed in insect cells *Biochem J* 1373, 423-435

24. Vlodaysky, I., Friedmann, Y., Elkin, M., Aingorn, H., Atzmon, R., Ishai-Michaeli, R., Bitan, M., Pappo, O., Peretz, T., Michal, I., Spector, L., and Pecker, I. (1999) Mammalian heparanase: gene cloning, expression and function in tumor progression and metastasis *Nat Med* 5, 793-802
25. Pikas, D. S., Li, J. P., Vlodaysky, I., and Lindahl, U. (1998) Substrate specificity of heparanases from human hepatoma and platelets *J Biol Chem* 273, 18770-18777
26. Gong, F., Jemth, P., Escobar Galvis, M. L., Vlodaysky, I., Horner, A., Lindahl, U., and Li, J. P. (2003) Processing of macromolecular heparin by heparanase *J Biol Chem* 278, 35152-35158
27. Balazs, E. A. (2004) Viscosupplementation for treatment of osteoarthritis: from initial discovery to current status and results *Surg Technol Int* 12, 278-289
28. Goa, K. L., and Benfield, P. (1994) Hyaluronic acid. A review of its pharmacology and use as a surgical aid in ophthalmology, and its therapeutic potential in joint disease and wound healing *Drugs* 47, 536-566
29. Stern, R. (2004) Hyaluronan catabolism: a new metabolic pathway *Eur J Cell Biol* 83, 317-325
30. DeAngelis, P. L., and White, C. L. (2002) Identification and molecular cloning of a heparosan synthase from *Pasteurella multocida* type D *J Biol Chem* 277, 7209-7213
31. Barzu, T., van Rijn, J. L., Petitou, M., Tobelem, G., and Caen, J. P. (1987) Heparin degradation in the endothelial cells *Thromb Res* 47, 601-609
32. Vann, W. F., Schmidt, M. A., Jann, B., and Jann, K. (1981) The structure of the capsular polysaccharide (K5 antigen) of urinary-tract-infective *Escherichia coli* 010: K5:H4. A polymer similar to desulfo-heparin *Eur J Biochem* 116, 359-364
33. Capila, I., and Linhardt, R. J. (2002) Heparin-protein interactions *Angew Chem Int Ed Engl* 41, 391-412
34. Tammi, M. I., Day, A. J., and Turley, E. A. (2002) Hyaluronan and homeostasis: a balancing act *J Biol Chem* 277, 4581-4584
35. Stern, R., Asari, A. A., and Sugahara, K. N. (2006) Hyaluronan fragments: an information-rich system *Eur J Cell Biol* 85, 699-715
36. Powell, J. D., and Horton, M. R. (2005) Threat matrix: low-molecular-weight hyaluronan (HA) as a danger signal *Immunol Res* 31, 207-218
37. West, D. C., and Kumar, S. (1989) Hyaluronan and angiogenesis *Ciba Found Symp* 143, 187-201; discussion 201-187, 281-185
38. Trochon, V., Mabilat, C., Bertrand, P., Legrand, Y., Smadja-Joffe, F., Soria, C., Delpech, B., and Lu, H. (1996) Evidence of involvement of CD44 in endothelial cell proliferation, migration and angiogenesis in vitro *Int J Cancer* 66, 664-668
39. Scheibner, K. A., Lutz, M. A., Boodoo, S., Fenton, M. J., Powell, J. D., and Horton, M. R. (2006) Hyaluronan fragments act as an endogenous danger signal by engaging TLR2 *J Immunol* 177, 1272-1281
40. Hodson, N., Griffiths, G., Cook, N., Pourhossein, M., Gottfridson, E., Lind, T., Lidholt, K., and Roberts, I. S. (2000) Identification that KfiA, a protein essential for the biosynthesis of the *Escherichia coli* K5 capsular polysaccharide, is an alpha -UDP-GlcNAc glycosyltransferase. The formation of a membrane-associated K5 biosynthetic complex requires KfiA, KfiB, and KfiC *J Biol Chem* 275, 27311-27315
41. Monheit, G. D., and Coleman, K. M. (2006) Hyaluronic acid fillers *Dermatol Ther* 19, 141-150
42. Li, M., Timmons, R. B., and Kinsel, G. R. (2005) Radio frequency plasma polymer coatings for affinity capture MALDI mass spectrometry *Anal Chem* 77, 350-353
43. Su, S. H., Chao, R. Y., Landau, C. L., Nelson, K. D., Timmons, R. B., Meidell, R. S., and Eberhart, R. C. (2003) Expandable bioresorbable endovascular stent. I. Fabrication and properties *Ann Biomed Eng* 31, 667-677
44. Bitter, T., and Muir, H. M. (1962) A modified uronic acid carbazole reaction *Anal Biochem* 4, 330-334
45. Lee, H. G., and Cowman, M. K. (1994) An agarose gel electrophoretic method for analysis of hyaluronan molecular weight distribution *Anal Biochem* 219, 278-287
46. Tracy, B. S., Avci, F. Y., Linhardt, R. J., and DeAngelis, P. L. (2007) Acceptor specificity of the *Pasteurella* hyaluronan and chondroitin synthases and production of chimeric glycosaminoglycans *J Biol Chem* 282, 337-344
47. Deangelis P L, White C L. (2004) Identification of a distinct, cryptic heparosan synthase from *Pasteurella multocida* types A, D, and F. *J Bacteriol.* 186, 8529-32.

What is claimed is:

1. A biomaterial composition, the composition comprising:

an isolated heparosan polymer, wherein the isolated heparosan polymer is biocompatible with a mammalian patient and is represented by the structure (-GlcUA-β1,4-GlcNAc-α-1,4-)$_n$, wherein the heparosan polymer is unsulfated, wherein at least a portion of the heparosan polymer is crosslinked, and wherein at least one of: n is about 1,000; and the molecular weight of the isolated heparosan polymer is in a range of from about 0.5 MDa to about 4.5 MDa.

2. The biomaterial composition of claim 1, wherein at least a portion of the heparosan polymer is linear.

3. The biomaterial composition of claim 1, wherein the composition is in a gel, semi-solid, and/or particulate state.

4. The biomaterial composition of claim 1, wherein the composition is in a liquid state.

5. The biomaterial composition of claim 1, wherein the composition is injectable and/or implantable.

6. The biomaterial composition of claim 1, wherein the composition is not susceptible to hyaluronidases and/or heparanases and thereby is not degraded in vivo.

7. A biomaterial composition, the composition comprising:

an isolated derivatized heparosan polymer, wherein the isolated derivatized heparosan polymer is biocompatible with a mammalian patient and is represented by the structure (-GlcUA-β1,4-GlcNAc-α-1,4-)$_n$, wherein n is a positive integer greater than or equal to 1, wherein the heparosan polymer is unsulfated, wherein the derivatized heparosan polymer is not found in nature, and wherein the heparosan polymer is derivatized by crosslinking at least a portion thereof.

8. The biomaterial composition of claim 7, wherein n is greater than 10.

9. The biomaterial composition of claim 7, wherein the composition is in a gel, semi-solid, and/or particulate state.

10. The biomaterial composition of claim 7, wherein the composition is in a liquid state.

11. The biomaterial composition of claim 7, wherein the composition is injectable and/or implantable.

12. The biomaterial composition of claim 7, wherein the composition is not susceptible to hyaluronidases and/or heparanases and thereby is not degraded in vivo.

* * * * *

UNITED STATES PATENT AND TRADEMARK OFFICE
CERTIFICATE OF CORRECTION

PATENT NO. : 9,629,914 B2  
APPLICATION NO. : 14/060077  
DATED : April 25, 2017  
INVENTOR(S) : Paul L. DeAngelis Page 1 of 1

It is certified that error appears in the above-identified patent and that said Letters Patent is hereby corrected as shown below:

In the Specification

Column 3, Line 25: Delete "(GAGS)" and replace with -- (GAGs) --

Column 4, Line 43: Delete "then" and replace with -- these --

Column 32, Line 32: After "Faseb" delete "16," and replace with -- J 6, --

Column 32, Line 66: After "Biochem J" delete "1373," and replace with -- 373, --

Column 33, Line 1: Delete "Vlodaysky," and replace with -- Vlodavsky, --

Column 33, Line 7: Delete "Vlodaysky," and replace with -- Vlodavsky, --

Column 33, Line 10: Delete "Vlodaysky," and replace with -- Vlodavsky, --

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*